US009802904B2

(12) United States Patent
Maloney et al.

(10) Patent No.: US 9,802,904 B2
(45) Date of Patent: Oct. 31, 2017

(54) INHIBITORS OF THE USP1/UAF1 DEUBIQUITINASE COMPLEX AND USES THEREOF

(71) Applicants: The United States of America, as represented by the Secretary, Department of Health and Human Services, Washington, DC (US); University of Delaware, Newark, DE (US)

(72) Inventors: David J. Maloney, Point of Rocks, MD (US); Andrew S. Rosenthal, Derwood, MD (US); Ajit Jadhav, Chantilly, VA (US); Thomas S. Dexheimer, Frederick, MD (US); Anton Simeonov, Bethesda, MD (US); Zhihao Zhuang, Wilmington, DE (US); Qin Liang, Elkton, MD (US); Diane K. Luci, Germantown, MD (US)

(73) Assignees: The United States of America, as represented by the Secretary, Department of Health and Human Services, Washington, DC (US); University of Delaware, Newark, DE (US)

( * ) Notice: Subject to any disclaimer, the term of this patent is extended or adjusted under 35 U.S.C. 154(b) by 0 days.

(21) Appl. No.: 14/655,538

(22) PCT Filed: Dec. 26, 2013

(86) PCT No.: PCT/US2013/077804

§ 371 (c)(1),
(2) Date: Jun. 25, 2015

(87) PCT Pub. No.: WO2014/105952

PCT Pub. Date: Jul. 3, 2014

(65) Prior Publication Data

US 2015/0344443 A1 Dec. 3, 2015

Related U.S. Application Data

(60) Provisional application No. 61/747,052, filed on Dec. 28, 2012.

(51) Int. Cl.

| | |
|---|---|
| ***A61K 31/505*** | (2006.01) |
| ***A61K 31/506*** | (2006.01) |
| ***C07D 239/42*** | (2006.01) |
| ***C07D 401/12*** | (2006.01) |
| ***C07D 401/14*** | (2006.01) |
| ***C07D 403/12*** | (2006.01) |
| ***C07D 239/94*** | (2006.01) |
| ***C07D 405/14*** | (2006.01) |
| ***C07D 405/12*** | (2006.01) |
| ***C07D 409/12*** | (2006.01) |
| ***C07D 471/04*** | (2006.01) |
| ***C07D 487/04*** | (2006.01) |
| ***C07D 491/048*** | (2006.01) |
| ***C07D 495/04*** | (2006.01) |

(52) U.S. Cl.
CPC ......... *C07D 239/94* (2013.01); *C07D 401/12* (2013.01); *C07D 401/14* (2013.01); *C07D 403/12* (2013.01); *C07D 405/12* (2013.01); *C07D 405/14* (2013.01); *C07D 409/12* (2013.01); *C07D 471/04* (2013.01); *C07D 487/04* (2013.01); *C07D 491/048* (2013.01); *C07D 495/04* (2013.01)

(58) Field of Classification Search
CPC .. C07D 239/42; C07D 401/12; C07D 401/14; C07D 403/12
See application file for complete search history.

(56) References Cited

U.S. PATENT DOCUMENTS

| | | | | |
|---|---|---|---|---|
| 7,820,704 | B2 * | 10/2010 | Mjalli | C07D 417/04 514/370 |
| 2007/0032499 | A1 | 2/2007 | Guedat et al. | |
| 2010/0286091 | A1 | 11/2010 | Wiestner et al. | |
| 2012/0077806 | A1 | 3/2012 | Donato et al. | |

FOREIGN PATENT DOCUMENTS

| | | | |
|---|---|---|---|
| EP | 1 254 903 | A1 | 11/2002 |
| EP | 2 360 158 | A1 | 8/2011 |
| JP | H06-192235 | A | 7/1994 |
| JP | 2002-530385 | A | 9/2002 |
| JP | 2003-026675 | A | 1/2003 |
| JP | 2005-520821 | A | 7/2005 |
| JP | 2006-502163 | A | 1/2006 |
| JP | 2008-526734 | A | 7/2008 |
| JP | 2010-505794 | A | 2/2010 |
| JP | 2010-208945 | A | 9/2010 |

(Continued)

OTHER PUBLICATIONS

Novel 2-(4-methylsulfonylphenyl)pyrimidine derivatives as highly potent and specific COX-2 inhibitors. Orjales et al. (Bioorganic & Medicinal Chemistry, 16, 2008, 2183-2199).*

(Continued)

*Primary Examiner* — Brian McDowell

(74) *Attorney, Agent, or Firm* — Leydig, Voit & Mayer, Ltd.

(57) ABSTRACT

Disclosed are inhibitors of the USP1/UAF1 deubiquitinase complex, for example. of formula (I), wherein $R^1$, $R^2$, and Q are as defined herein, which are useful in treating diseases such as cancer, and improving the efficacy of DNA damaging agents in cancer treatment. Also disclosed is a composition comprising a pharmaceutically suitable carrier and at least one compound of the invention, a method of method of inhibiting a heterodimeric deubiquitinase complex in a cell, and a method of enhancing the chemotherapeutic treatment of cancer in a mammal undergoing treatment with an anti cancer agent. Further disclosed is a method of preparing compounds of the invention.

4 Claims, 5 Drawing Sheets

(56) References Cited

FOREIGN PATENT DOCUMENTS

| | | | |
|---|---|---|---|
| JP | 2011-032169 | A | 2/2011 |
| JP | 2013-500255 | A | 1/2013 |
| JP | 2014-517492 | A | 3/2014 |
| JP | 2014-237590 | A | 12/2014 |
| WO | 1993/007124 | A1 | 4/1993 |
| WO | WO 03026661 | * | 4/2003 |
| WO | WO 03/049739 | A1 | 6/2003 |
| WO | WO 03/077656 | A1 | 9/2003 |
| WO | WO 2005/103022 | A1 | 11/2005 |
| WO | 2006/004589 | A2 | 1/2006 |
| WO | 2006/071095 | A1 | 7/2006 |
| WO | WO 2008/040753 | A1 | 4/2008 |
| WO | WO 2011/011522 | A2 | 1/2011 |
| WO | WO 2011/026835 | A1 | 3/2011 |
| WO | WO 2011/094545 | A2 | 8/2011 |
| WO | WO 2011101161 | * | 8/2011 |
| WO | 2011/140527 | A2 | 11/2011 |
| WO | WO 2011/137320 | A2 | 11/2011 |
| WO | WO 2012/012712 | A2 | 1/2012 |
| WO | WO 2012/061754 | A2 | 5/2012 |
| WO | 2012/172043 | A1 | 12/2012 |
| WO | WO 2013/004332 | A1 | 1/2013 |
| WO | WO 2013/030218 | A1 | 3/2013 |
| WO | WO 2013/058691 | A1 | 4/2013 |
| WO | WO 2013/112651 | A2 | 8/2013 |
| WO | WO 2013/112699 | A2 | 8/2013 |
| WO | WO 2013/112706 | A1 | 8/2013 |
| WO | WO 2014/105952 | A2 | 7/2014 |

OTHER PUBLICATIONS

Albertella et al., "A role for polymerase η in the cellular tolerance to cisplatin-induced damage," *Cancer Res.*, 65 (21), 9799-9806 (2005).

Altun et al., "Activity-based chemical proteomics accelerates inhibitor development for deubiquitylating enzymes," *Chem. Biol.*, 18 (11), 1401-1412 (2011).

Borodovsky et al., "Chemistry-based functional proteomics reveals novel members of the deubiquitinating enzyme family," *Chem. Biol.* 9 (10), 1149-1159 (2002).

Chauhan et al., "A small molecule inhibitor of ubiquitin-specific protease-7 induces apoptosis in multiple myeloma cells and overcomes bortezomib resistance," *Cancer Cell*, 22 (3) , 345-358 (2012).

Chen et al., "Selective and Cell-Active Inhibitors of the USP1/UAF1 Deubiquitinase Complex Reverse Cisplatin Resistance in Non-small Cell Lung Cancer Cells," *Chem. Biol.*, 18 (11), 1390-1400 (2011).

Chou, "Drug combination studies and their synergy quantification using the Chou-Talalay Method," *Cancer Res.*, 70 (2), 440-446 (2010).

Colland et al., "Small-molecule inhibior of USP7/HAUSP ubiquitin protease stabilizes and activates p53 in cells," *Mol. Cancer Ther.*, 8 (8), 2286-2295 (2009).

Colland, "The therapeutic potential of deubiquitinating enzyme inhibitors," *Biochem. Soc. Trans.*, 38 (Pt 1), 137-143 (2010).

Colombo et al., "Synthesis and biological evaluation of 9-oxo-9H-indeno[1,2-b]pyrazine-2,3-dicarbonitrile analogues as potential inhibitors of deubiquitinating enzymes," *Chem. Med. Chem.*, 5 (4), 552-558 (2010).

Coombs et al., "Small-molecule pyrimidine inhibitors of the cdc2-like (Clk) and dual specificity tyrosine phosphorylation-regulated (Dyrk) kinases: development of chemical probe ML315," *Bioorg. Med. Chem. Lett.*, 23 (12), 3654-3661 (2013).

Dexheimer et al., "Synthesis and structure-activity relationship studies of N-benzyl-2-phenylpyrimidin-4-amine derivatives as potent USP1/UAF1 deubiquitinase inhibitors with anticancer activity against nonsmall cell lung cancer," *J. Med. Chem.*, 57 (19), 8099-8110 (2014).

Ding et al., "A combinatorial scaffold approach toward kinase-directed heterocycle libraries," *J. Am. Chem. Soc.*, 124 (8), 1594-1596 (2002).

Fujiwara et al., "Preparation of 4-aminopyrimidine derivatives as IKK2 inhibitors," Database Caplus Chemical Abstracts Services, Database Accession No. 2011:199450.

International Preliminary Report on Patentability, Application No. PCT/US2013/077804, date mailed Jun. 30, 2015.

International Search Report, Application No. PCT/US2013/077804, date mailed Jul. 22, 2014.

Köberle et al., "Cisplatin resistance: preclinical findings and clinical implications," *Biochim. Biophys. Acta.*, 1802 (2), 172-182 (2010).

Kokubo et al., "Preparation of heterocyclic compounds as CCR4 or TARC and/or MDC function regulators," Database Caplus Chemical Abstract Service, Database Accession No. 2010:1193251.

Lee et al., "Enhancement of proteasome activity by a small-molecule inhibitor of USP14," *Nature*, 467 (7312), 179-184 (2011).

Ma et al., "Combinatorial synthesis of substituted biaryls and heterocyclic arylamines," *J. Comb. Chem.*, 6 (3), 426-430 (2004).

Miyata et al., "Orally available pyridinylpyrimidine derivatives as novel RANKL-induced osteoclastogenesis inhibitors," *Bioorg. Med. Chem. Lett.*, 22 (17), 5681-5684 (2012).

Mohamed et al., "Design, synthesis and structure-activity relationship (SAR) studies of 2,4-disubstituted pyrimidine derivatives: dual activity as cholinesterase and Aβ-aggregation inhibitors," *Bioorg. Med. Chem.*, 19 (7), 2269-2281 (2011).

Sato et al., "2-(Pyridin-2-yl)pyrimidin-4-amine compound and salt thereof, and their use for pharmaceutical composition for treatment of disease related to RANKI/RANK signals," Database Caplus Chemical Abstract Service, Database Accession No. 2013:516354.

Tian et al., "Characterization of selective ubiquitin and ubiquitin-like protease inhibitors using a fluorescence-based multiplex assay format," *Assay Drug Dev. Technol.*, 9 (2), 165-173 (2011).

Weinstock et al., "Selective Dual Inhibitors of the Cancer-Related Deubiquitylating Proteases USP7 and USP47," *ACS Med. Chem. Lett.*, 3(10), 789-792 (2012).

Written Opinion of the International Searching Authority, Application No. PCT/US2013/077804, date mailed Jul. 22, 2014.

Xiang et al., "Synthesis and Biological Examination of New Pyrimidine Type Derivatives as Potential Phosphodiesterase (PDE) V Inhibitors," *Cheminform*, 29 (47), 1998.

Xiao et al., "Insights into the mechanism of microtubule stabilization by Taxol," *Proc. Natl. Acad. Sci. U.S.A.*, 103 (27), 10166-10173 (2006).

Yonetoku et al., "Preparation of 4-aminopyrimidine derivatives as insulin secretion accelerators," Database Caplus Chemical Abstract Service, Database Accession No. 2003:261678.

Japanese Patent Office, Office Action issued in Application No. 550767/2015, dated Jul. 25, 2017, 17 pages.

* cited by examiner

INHIBITORS OF THE USP1/UAF1 DEUBIQUITINASE COMPLEX AND USES THEREOF

CROSS-REFERENCE TO A RELATED APPLICATION

This application is a U.S. National Phase of International Patent Application No. PCT/US2013/077804, filed Dec. 26, 2013, which claims the benefit of U.S. Provisional Patent Application No. 61/747,052, filed Dec. 28, 2012, the disclosures of which are incorporated by reference.

BACKGROUND OF THE INVENTION

Ubiquitin is a small, highly conserved protein composed of 76 amino acids that is post-transcriptionally attached to target proteins, including itself, via a concerted three-step enzymatic reaction. This covalent linkage or isopeptide bond primarily occurs between the C-tenninal glycine of ubiquitin and the ϵ-amino group of lysine residue(s) on the target protein (Pickart, C. M., *Annu. Rev. Biochem.,* 2001: 503-33). The functional consequence of ubiquitination is determined by the number and linkage topology of ubiquitin molecules conjugated to the target protein. For example, proteins exhibiting Lys48-linked polyubiquitin chains are generally targeted to the proteasome for degradation, while monoubiquitination or polyubiquitin chains linked through other lysines regulate several non-proteolytic functions, including cell cycle regulation (Nakayama, K. I. et al., *Nat. rev. Cancer*, 6(5): 369-81 (2006)), DNA repair (Bergink, S., et al., Nature 458(7237): 461-7 (2009)), transcription (Conaway, R. C., et al., *Science* 296(5571): 1254-8 (2002)), and endocytosis (Mukhopadhyay, D., et al., *Science* 315(5809): 201-5 (2007)). Similar to other posttranslational modifications, ubiquitination is a reversible process counteracted by a family of enzymes known as deubiquitinases (DUBs). These enzymes are cysteine proteases or metalloproteases that hydrolyze the ubiquitin isopeptide bond (Komander, D., et al., *Nat. Rev. Mol. Cell Biol.* 10(8): 550-63 (2007)). The human genome encodes close to 100 DUBs.

In recent years, the ubiquitin-proteasome system has attracted increasing attention as a novel drug target. DUBs have been recognized as attractive targets for drug discovery since several members of the DUB family have been implicated in processes related to human disease, including cancer and neurodegeneration. Among them, USP1 (ubiquitin-specific protease 1) has gained increased interest as a novel therapeutic target given its roles in DNA damage response. The interaction of USP1 with UAF1 (USP1-associated factor 1), a WD40 repeat-containing protein, leads to the formation of an activated USP1/UAF1 complex, which is required for the deubiquitinase activity. The USP1/UAF1 complex has been found to deubiquitinate monoubiquitinated PCNA (proliferating cell nuclear antigen) and monoubiquitinated FANCD2 (Fanconi anemia group complementation group D2), which are proteins that play important functions in translesion synthesis (TLS) and the Fanconi anemia (FA) pathway, respectively. These two pathways are essential for repair of DNA damage induced by DNA cross-linking agents, such as cisplatin and mitomycin C (MMC). Previous studies have demonstrated that disruption of USP1 or UAF1 in chicken DT40 cells resulted in increased sensitivity to DNA cross-linkers. In addition, knockout of the murine USP1 gene in a mouse model resulted in hypersensitivity to MMC. It also has been demonstrated that inhibiting the cellular activity of human USP1 by pharmacologically active small molecules sensitized non-small cell lung cancer (NSCLC) cells to cisplatin.

The compounds GW7647 and Pimozide have been described as inactivators of USP1. However, both of these compounds are limited by potency and off-target pharmacology, in part because both of these compounds have annotated activity against unrelated targets. Another inhibitor of USP1, C527, which was reported by D'Andrea et al. in WO 2011/137320 A1, sensitizes cells to both the cross-linking agent, mitomycin C, and the topoisomerase I inhibitor, camptothecin. However, C527 shows low micromolar inhibition of related USPs as well as dissimilar DUBs (i.e., UCL-H1 and UCL-H3).

The foregoing shows that there exists an unmet need for new selective inhibitors of the USP1/UAF1 complex, and thus, agents for treating and/or potentiating diseases amenable to treatment or to improvement of treatment, for example, cancer.

BRIEF SUMMARY OF THE INVENTION

The invention provides a compound of formula (I):

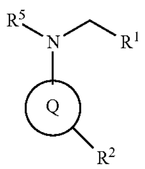

(I)

wherein Q is an optionally substituted heteroaryl group, wherein $R^1$ is selected from aryl, heteroarylaryl, heteroaryl, and heterocyclyl, wherein aryl, heteroarylaryl, heteroaryl, and heterocyclyl are optionally substituted with 1 to 5 substituents selected from halo, alkyl, alkoxy, trifluoromethyl, cyano, aryl, optionally substituted aryl, optionally substituted heteroaryl, heterocyclyl, methylenedioxy, and cycloalkyl, $R^2$ is selected from aryl, heteroaryl, and heterocyclyl, wherein aryl is optionally substituted with halo, alkyl, cycloalkyl, alkoxy, hydroxyalkyl, alkylthio, nitro, heterocyclyl, and alkylcarbonyl, wherein alkyl is optionally substituted with 1-3 fluoro substituents, and $R^5$ is hydrogen or optionally substituted alkyl, a deuterated derivative thereof, or a pharmaceutically acceptable salt thereof.

The invention also provides a pharmaceutical composition comprising a compound or salt of the invention and a pharmaceutically acceptable carrier.

The invention further provides a method of inhibiting a heterodimeric deubiquitinase complex in a cell, comprising administering to the cell an effective amount of a compound or salt of the invention.

The invention additionally provides a method of enhancing the chemotherapeutic treatment of cancer in a mammal undergoing treatment with an anti-cancer agent, comprising co-administering to the mammal an effective amount of a compound or salt of the invention.

The invention further provides a method of treating cancer in a mammal in need thereof, comprising administering to the mammal an effective amount of a compound or salt of the invention.

The invention also provides a method of synthesizing a compound of formula (II):

(II)

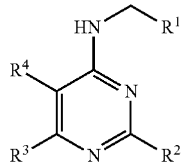

wherein $R^1$ is selected from aryl, heteroarylaryl, heteroaryl, and heterocyclyl, wherein aryl, heteroarylaryl, heteroaryl, and heterocyclyl are optionally substituted with 1 to 5 substituents selected from halo, alkyl, alkoxy, trifluoromethyl, cyano, aryl, optionally substituted aryl, optionally substituted heteroaryl, heterocyclyl, methylenedioxy, and cycloalkyl, wherein $R^2$ is selected from aryl, heteroaryl, heterocyclyl, amino, and dialkylamino, wherein aryl is optionally substituted with halo, alkyl, cycloalkyl, alkoxy, hydroxyalkyl, alkylthio, nitro, heterocyclyl, and alkylcarbonyl, wherein alkyl is optionally substituted with 1-3 fluoro substituents, $R^3$ is selected from hydrogen and alkyl, and $R^4$ is selected from hydrogen, alkyl, alkoxy, amino, alkylamino, dialkylamino, alkylthio, and halo, comprising the steps of:

(i) reacting a compound of the formula

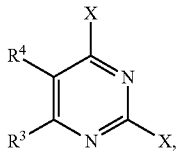

wherein X is a leaving group, with a compound of the formula $H_2N—CH_2—R^1$ to form a compound of the formula

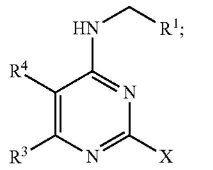

and (ii) reacting the compound of formula

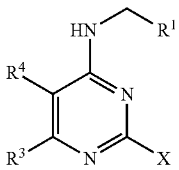

with a compound of the formula $R_2—B(OH)_2$ to form the compound of formula (II).

Among the human USPs, USP1 occupies a special position as it has been implicated in DNA damage response. Because USP1 plays important roles in the two essential DNA damage response pathways, it represents a promising target for small molecule intervention to improve the efficacy of the commonly used DNA damaging drugs by modulating cells' ability of repairing or tolerating DNA lesions. The compounds of the invention exhibit selectivity for USP1/UAF1 versus USP2, USP5, USP7, USP8, and USP 12/46.

BRIEF DESCRIPTION OF THE SEVERAL VIEWS OF THE DRAWING(S)

Figure 3A:
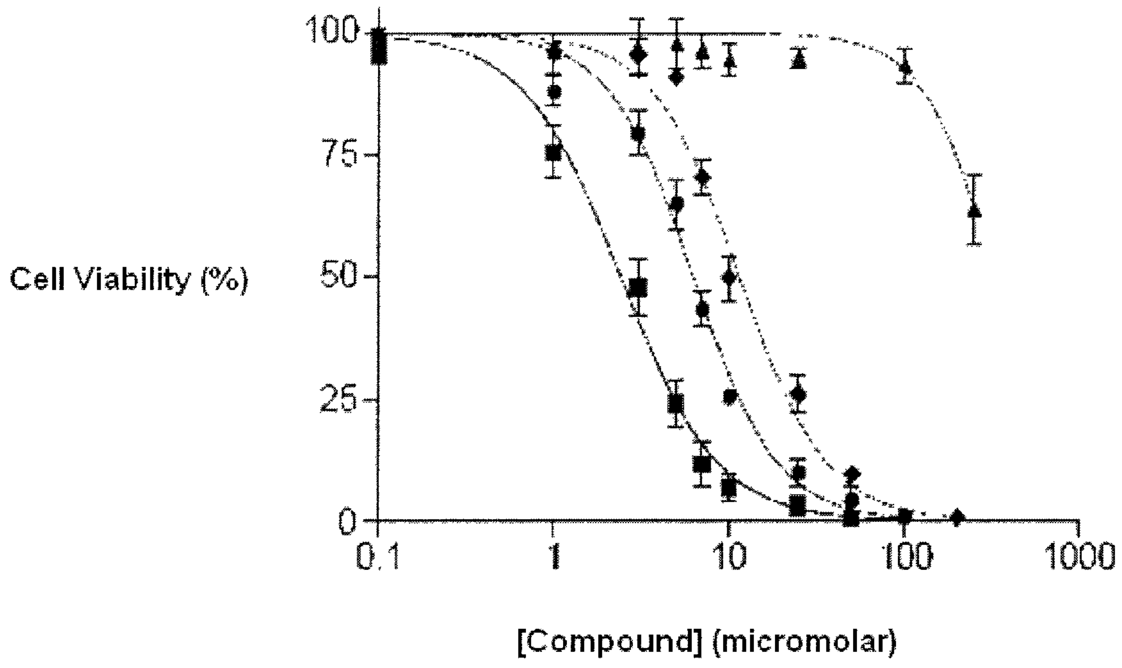

FIG. 3A illustrates the cytotoxicity in H596 cells exhibited by cisplatin alone (diamond), compound 81 (triangle), cisplatin plus compound 81 at a 1:1 ratio (circle), and cisplatin plus compound 81 at a 1:4 ratio (square).

Figure 3B:
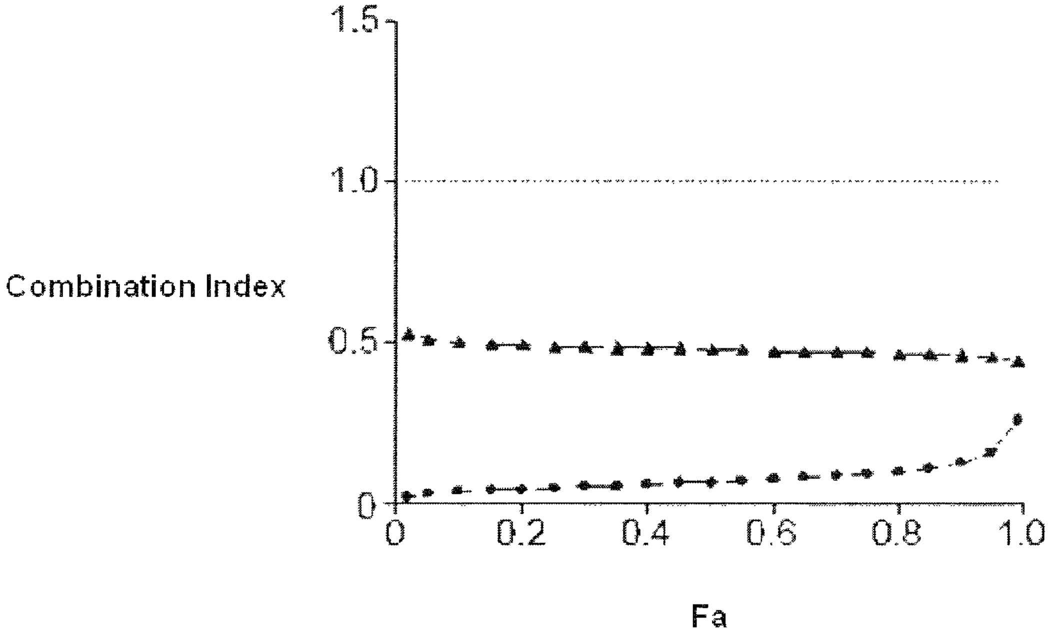

FIG. 3B illustrates the combination index analysis on cytotoxicity with ratios of cisplatin and compound 81 at a 1:1 ratio as circles, and cisplatin plus compound 81 at a 1:4 ratio as squares. The dashed line represents a combination index=1.

Figure 3C:
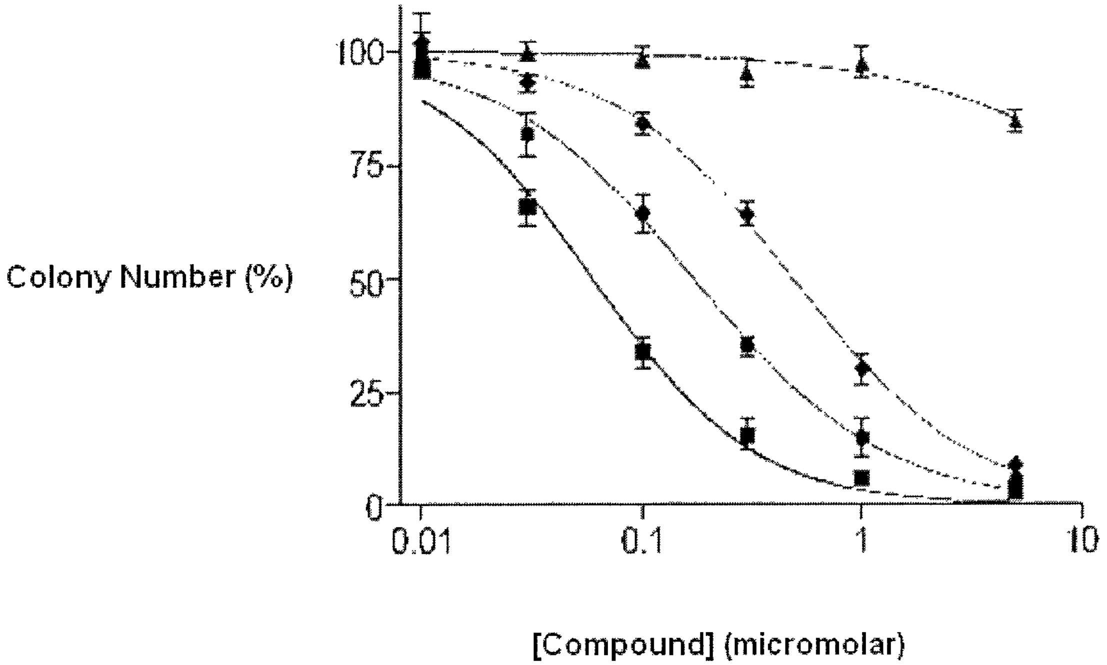

FIG. 3C illustrates the effect on colony number in H596 cells exhibited by cisplatin alone (diamond), compound 81 (triangle), cisplatin plus compound 81 at a 1:1 ratio (circle), and cisplatin plus compound 81 at a 1:4 ratio (square).

Figure 3D:
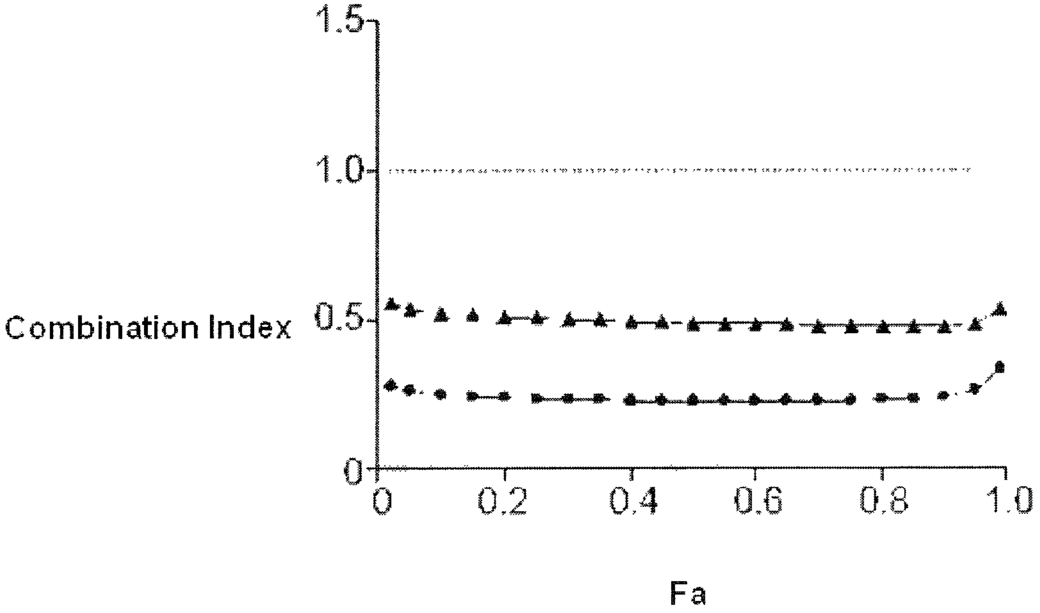

FIG. 3D illustrates the combination index analysis of effect on colony number with ratios of cisplatin and compound 81 at a 1:1 ratio as circles, and cisplatin plus compound 81 at a 1:4 ratio as squares. The dashed line represents a combination index=1.

DETAILED DESCRIPTION OF THE INVENTION

In an embodiment, the invention provides a compound of formula (I):

(I)

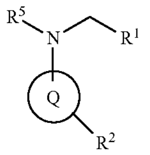

wherein Q is an optionally substituted heteroaryl group, wherein $R^1$ is selected from aryl, heteroarylaryl, heteroaryl, and heterocyclyl, wherein aryl, heteroarylaryl, heteroaryl, and heterocyclyl are optionally substituted with 1 to 5 substituents selected from halo, alkyl, alkoxy, trifluoromethyl, cyano, aryl, optionally substituted aryl, optionally substituted heteroaryl, heterocyclyl, methylenedioxy, and cycloalkyl, $R^2$ is selected from aryl, heteroaryl, and heterocyclyl, wherein aryl is optionally substituted with halo, alkyl, cycloalkyl, alkoxy, hydroxyalkyl, alkylthio, nitro, heterocyclyl, and alkylcarbonyl, wherein alkyl is optionally substituted with 1-3 fluoro substituents, and $R^5$ is hydrogen or optionally substituted alkyl, a deuterated derivative thereof, or a pharmaceutically acceptable salt thereof.

In accordance with certain embodiments, Q is selected from

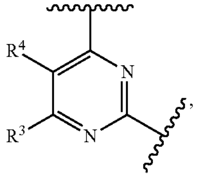, 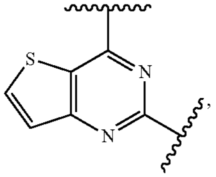,

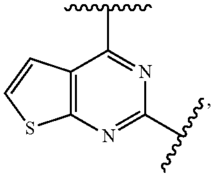, 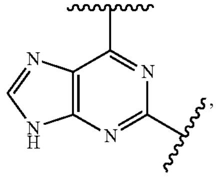,

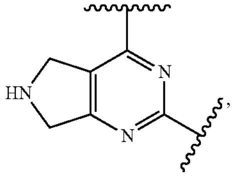, 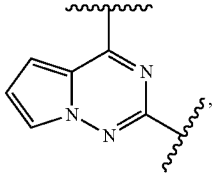,

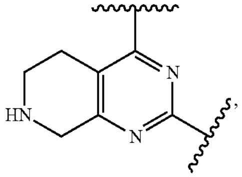, 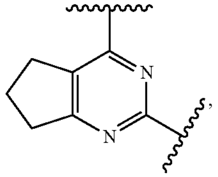,

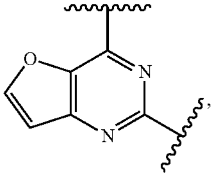, and 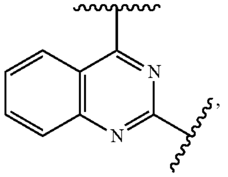, wherein $R^1$ is selected from aryl, heteroarylaryl, heteroaryl, and heterocyclyl, wherein aryl, heteroarylaryl, heteroaryl, and heterocyclyl are optionally substituted with 1 to 5 substituents selected from halo, alkyl, alkoxy, trifluoromethyl, cyano, aryl, optionally substituted aryl, optionally substituted heteroaryl, heterocyclyl, methylenedioxy, and cycloalkyl, $R^2$ is selected from aryl, heteroaryl, and heterocyclyl, wherein aryl is optionally substituted with halo, alkyl, cycloalkyl, alkoxy, hydroxyalkyl, alkylthio, nitro, heterocyclyl, and alkylcarbonyl, wherein alkyl is optionally substituted with 1-3 fluoro substituents, $R^3$ is selected from hydrogen and alkyl, and $R^4$ is selected from hydrogen, alkyl, alkoxy, amino, alkylamino, dialkylamino, alkylthio, and halo, or a pharmaceutically acceptable salt thereof.

In accordance with an embodiment, Q is

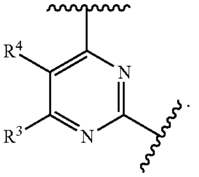.

In accordance with any of the above embodiments, $R^3$ is selected from hydrogen and methyl.

In accordance with any of the above embodiments, $R^5$ is hydrogen.

In accordance with any of the above embodiments, $R^4$ is selected from hydrogen, methyl, methoxy, amino, dimethylamino, methylthio, and halo.

In accordance with certain embodiments, Q is selected from

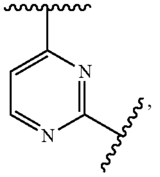, 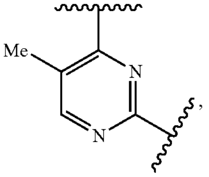,

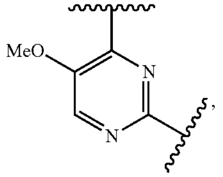, 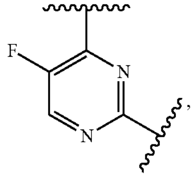,

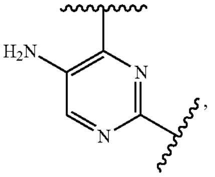, 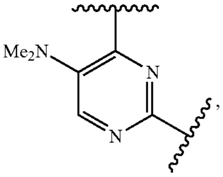,

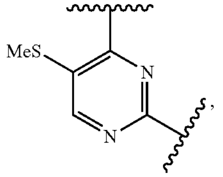, 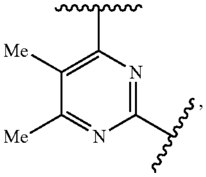, and

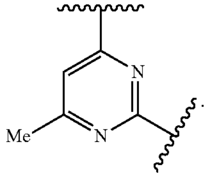.

In accordance with any of the above embodiments, $R^1$ is selected from:

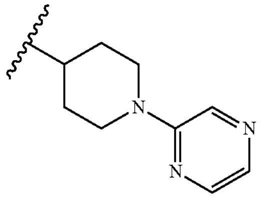, 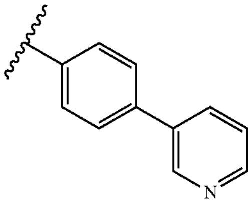,

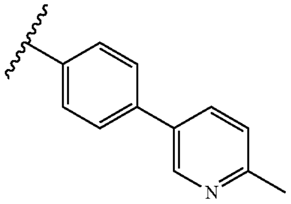, 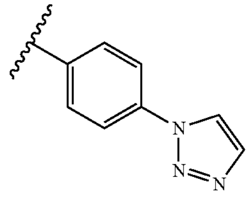,

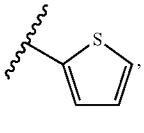, 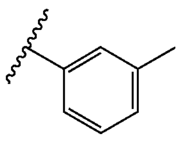, 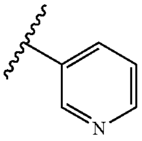,

-continued
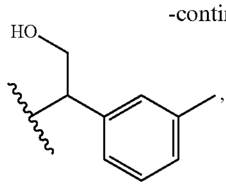,
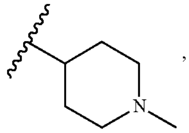,
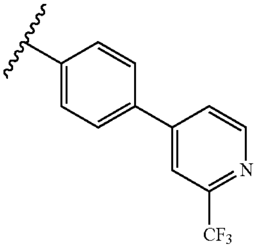,
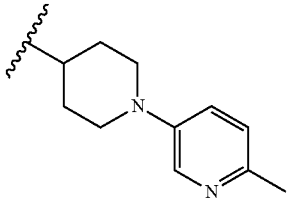,
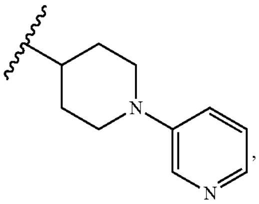,
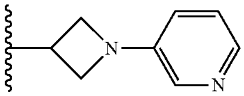,
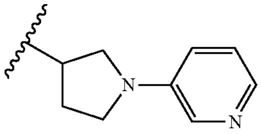,
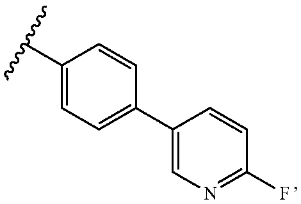,
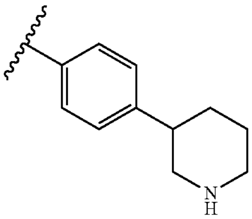,
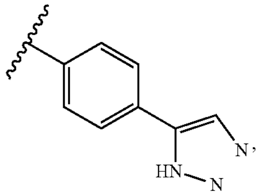,
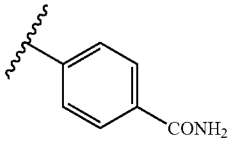,
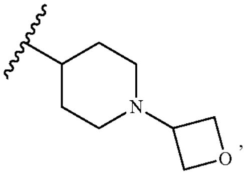,
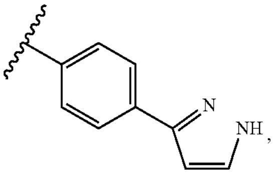,
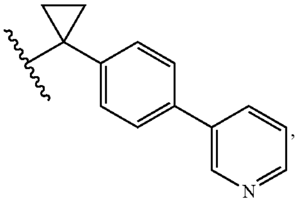, and
-continued
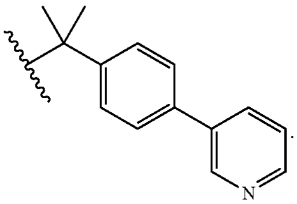.
In accordance with any of the above embodiments, $R^2$ is selected from:
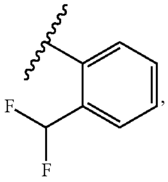,
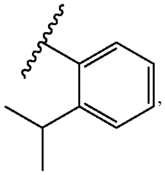,
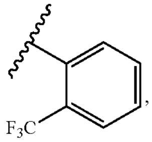,
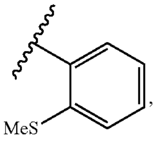,
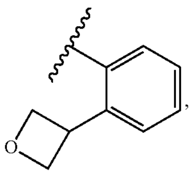,
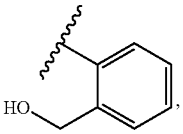,
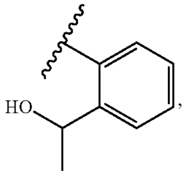,
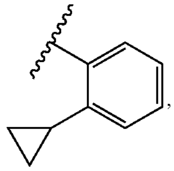, and
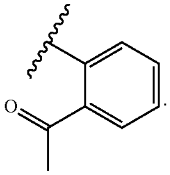.
In accordance with certain embodiments, Q is
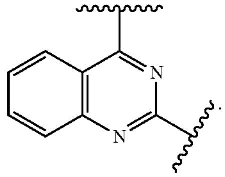 [SMILES: *c1nc(*)c2ccccc2n1].
In accordance with certain embodiments, $R^1$ is selected from
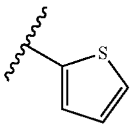,
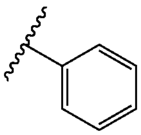,
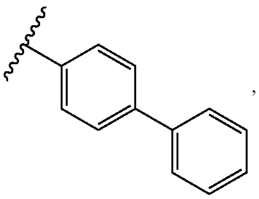, -continued
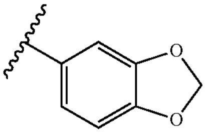,
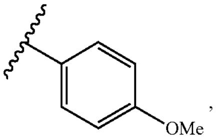,
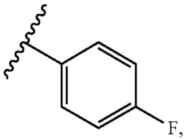,
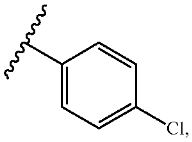,
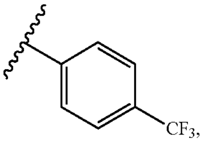,
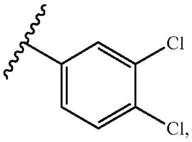,
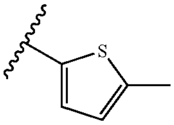,
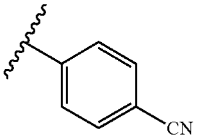,
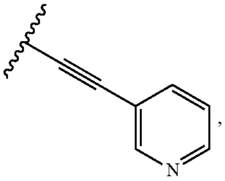,
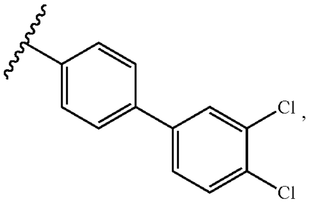,
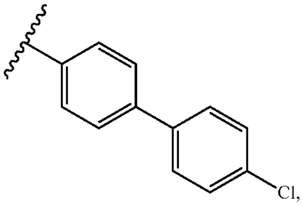,
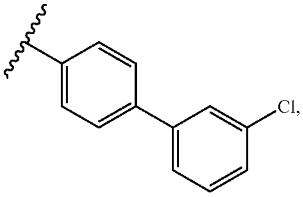,
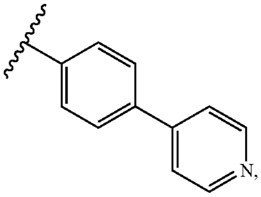,
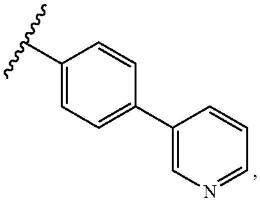,
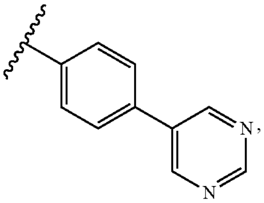,
-continued
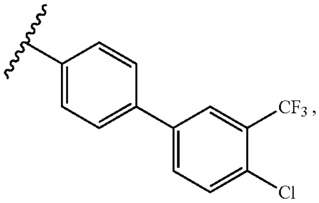,
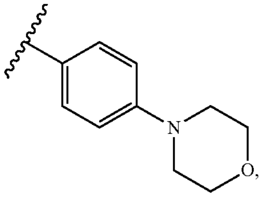,
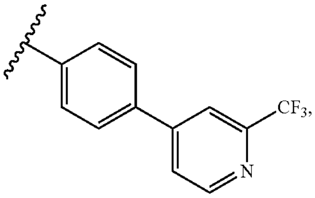, and
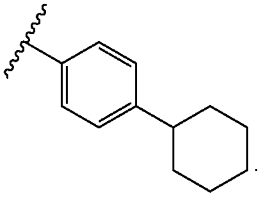.
In accordance with certain embodiments, $R^2$ is selected from
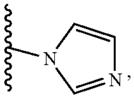,
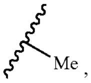,
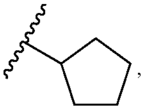,
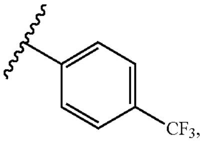,
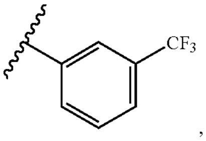,
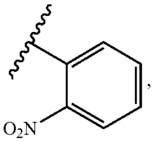,
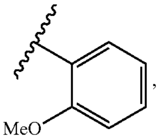,
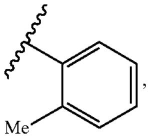,
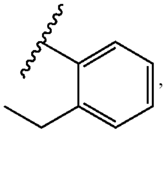,
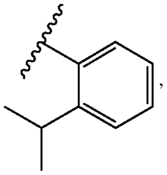,
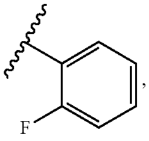,
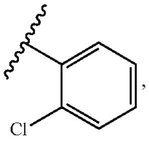,
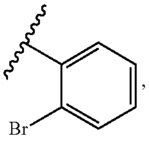,
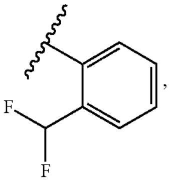, and -continued
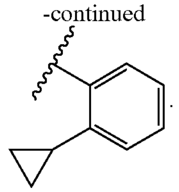
In accordance with certain embodiments, Q is selected from
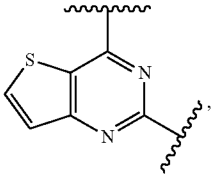, 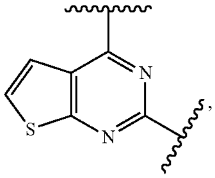,
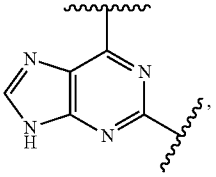, 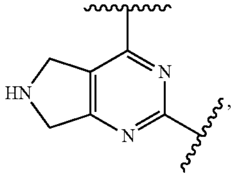,
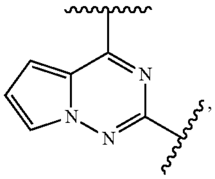, 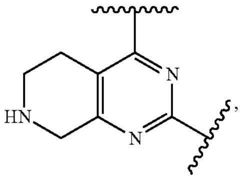,
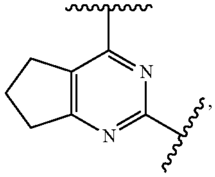, and 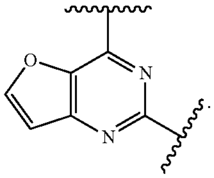
In accordance with a certain preferred embodiment, $R^1$ is
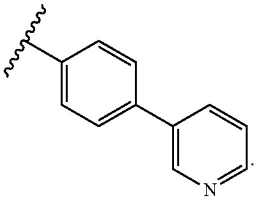 [SMILES: *c1ccc(-c2cccnc2)cc1]
In accordance with a certain preferred embodiment, $R^2$ is
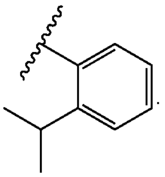 [SMILES: *c1ccccc1C(C)C]
In accordance with certain embodiments, Q is
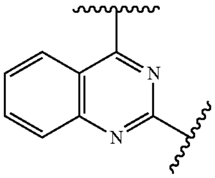, $R^2$ is 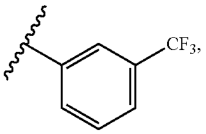 and
-continued
$R^1$ is 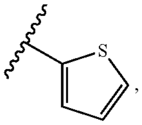, 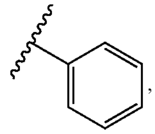,
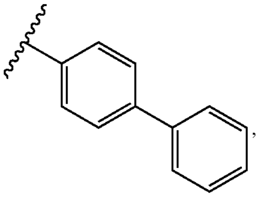, 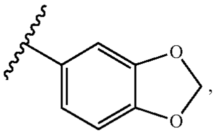,
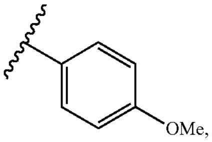 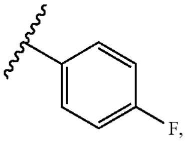
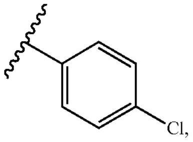 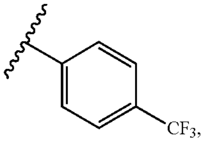
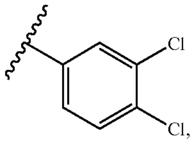 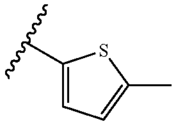,
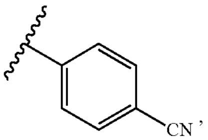 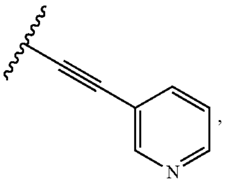,
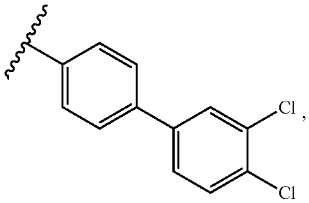
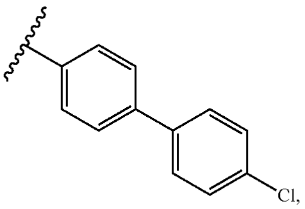
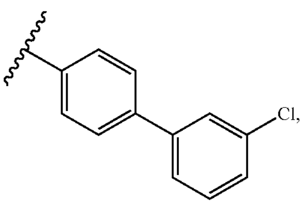 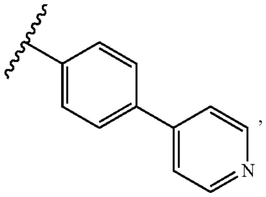, -continued
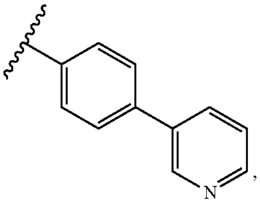, 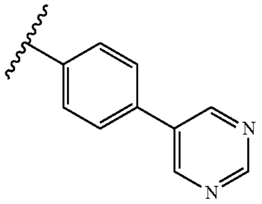,
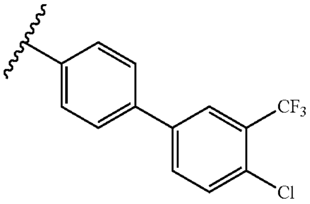,
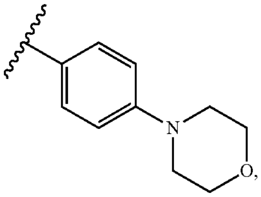,
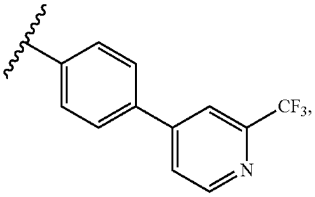, or
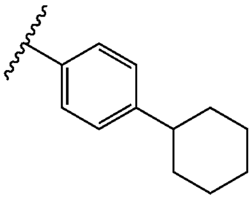.
In accordance with certain embodiments, Q is
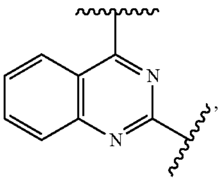 [SMILES: *c1nc(*)c2ccccc2n1],
$R^1$ is
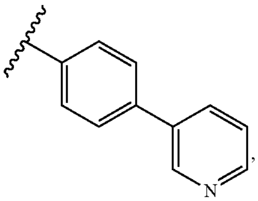,
and $R^2$ is
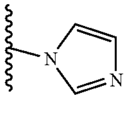, 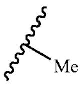, 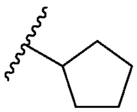,
-continued
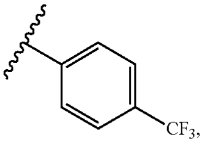, 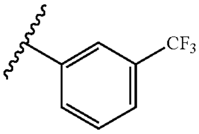,
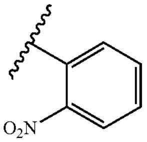, 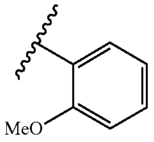, 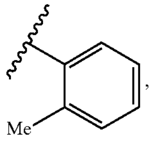,
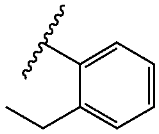, 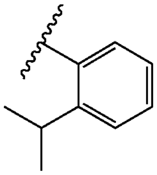, 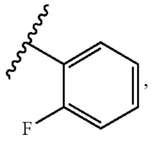,
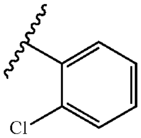, 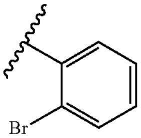, or
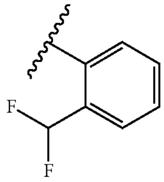.
In certain preferred embodiments, Q is
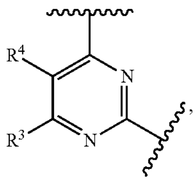, $R^1$ is 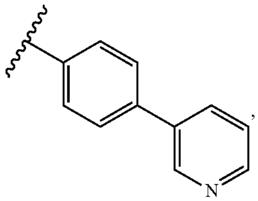 [SMILES: *c1ccc(-c2cccnc2)cc1],
$R^3$ is hydrogen, $R^4$ is methyl, and $R^2$ is
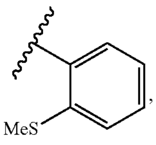, 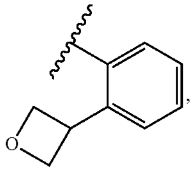, 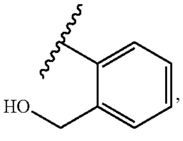,
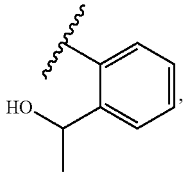, 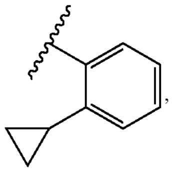, or
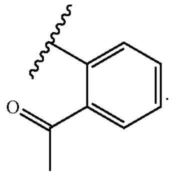.

In certain preferred embodiments, $R^1$ is

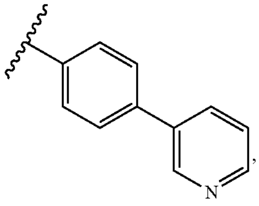 [SMILES: *c1ccc(-c2cccnc2)cc1]

, $R^2$ is

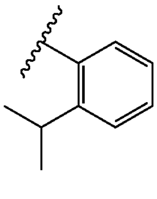

, and Q is

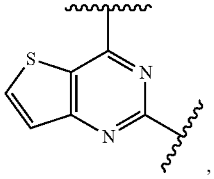

,

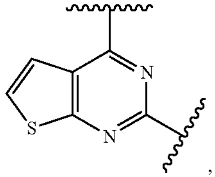

,

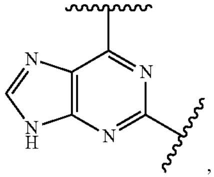

,

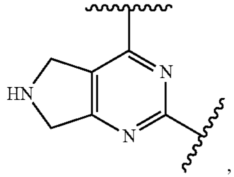

,

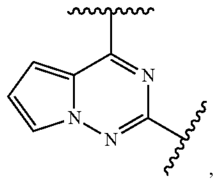

,

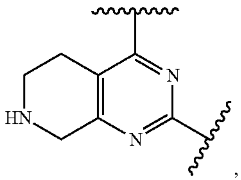

,

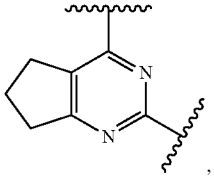

, or

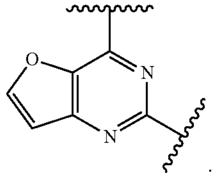

.

In accordance with any of the above embodiments, the nitrogen atom and $R^2$ are preferably attached to the pyrimidine ring of Q as follows:

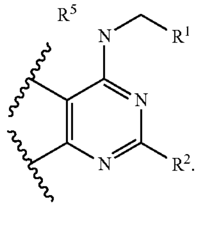

Specific examples of compounds of the invention are set forth in Tables 1-4 infra.

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tort-butyl, pentyl, isoamyl, hexyl, and the like.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups such as methyl groups, ethyl groups, and the like.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be any suitable heterocyclyl group and can be an aliphatic heterocyclyl group, an aromatic heterocyclyl group, or a combination thereof. The heterocyclyl group can be a monocyclic heterocyclyl group or a bicyclic heterocyclyl group. Suitable heterocyclyl groups include morpholine, piperidine, tetrahydrofuryl, oxetanyl, pyrrolidinyl, and the like. Suitable bicyclic heterocyclyl groups include monocytic heterocyclyl rings fused to a $C_6$-$C_{10}$ aryl ring. When the heterocyclyl group is a bicyclic heterocyclyl group, both ring systems can be aliphatic or aromatic, or one ring system can be aromatic and the other ring system can be aliphatic as in, for example, dihydrobenzofuran. The term "heteroaryl" refers to a monocyclic or bicyclic 5- or 6-membered ring system as described herein, wherein the heteroaryl group is unsaturated and satisfies Hackers rule. Non-limiting examples of suitable heteroaryl groups include furanyl, thiopheneyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiopheneyl, indolyl, quinolinyl, isoquinolinyl, benzimidazolyl, benzoxazolinyl, benzothiazolinyl, and quinazolinyl. The heterocyclyl or heteroaryl group is optionally substituted with 1, 2, 3, 4, or 5 substituents as recited herein such as with alkyl groups such as methyl groups, ethyl groups, and the like, or with aryl groups such as phenyl groups, naphthyl groups and the like, wherein the aryl groups can be further substituted with, for example halo, dihaloalkyl, trihaloalkyl, nitro, hydroxy, alkoxy, aryloxy, amino, substituted amino, alkylcarbonyl, alkoxycarbonyl, arylcarbonyl, aryloxycarbonyl, thio, alkylthio, arylthio, and the like, wherein the optional substituent can be present at any open position on the heterocyclyl or heteroaryl group.

The term "alkylcarbonyl," as used herein, refers to an alkyl group linked to a carbonyl group and further linked to a molecule via the carbonyl group, e.g., alkyl-C(=O)—. The term "alkoxycarbonyl," as used herein, refers to an alkoxy group linked to a carbonyl group and further linked to a molecule via the carbonyl group, e.g., alkyl-O—C(=O)—.

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2 π electrons, according to Hückel's Rule.

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445, and *Journal of Pharmaceutical Science*, 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (e.g., a dimethylaminoalkyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

Chemistry

The invention provides a method of synthesizing a compound of formula (II):

(II)

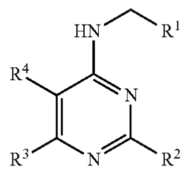

wherein $R^1$ is selected from aryl, heteroarylaryl, heteroaryl, and heterocyclyl, wherein aryl, heteroarylaryl, heteroaryl, and heterocyclyl are optionally substituted with 1 to 5 substituents selected from halo, alkyl, alkoxy, trifluoromethyl, cyano, aryl, optionally substituted aryl, optionally substituted heteroaryl, heterocyclyl, methylenedioxy, and cycloalkyl, wherein $R^2$ is selected from aryl, heteroaryl, heterocyclyl, amino, and dialkylamino, wherein aryl is optionally substituted with halo, alkyl, cycloalkyl, alkoxy, hydroxyalkyl, alkylthio, nitro, heterocyclyl, and alkylcarbonyl, wherein alkyl is optionally substituted with 1-3 fluoro substituents, $R^3$ is selected from hydrogen and alkyl, and $R^4$ is selected from hydrogen, alkyl, alkoxy, amino, alkylamino, dialkylamino, alkylthio, and halo, comprising the steps of:

(i) reacting a compound of the formula

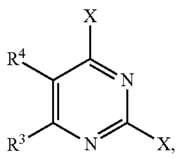

wherein X is a leaving group, with a compound of the formula $H_2N—CH_2—R^1$ to form a compound of the formula

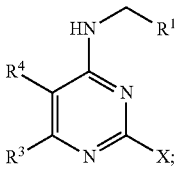

and (ii) reacting the compound of formula

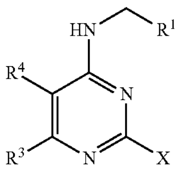

with a compound of the formula $R_2—B(OH)_2$ to form the compound of formula (II).

The synthesis of compounds of the invention can be performed as illustrated for an embodiment of the invention. Amination of 2,4-dichloro-5-methylpyrimidine with 4-iodobenzyl amine in the presence of a base such as triethylamine in a solvent such as chloroform provided the aminated pyrimidine 100. Sonogashira coupling of propolic acid in the presence of sodium azide, 20 mol % L-proline, 20 mol % sodium ascorbate, 10 mol % cupric sulfate, and 1.2 eq potassium carbonate in DMSO provided the triazolyl compound 101. Coupling of compound 101 with 2-isopropylphenylboronic acid gave compound 82.

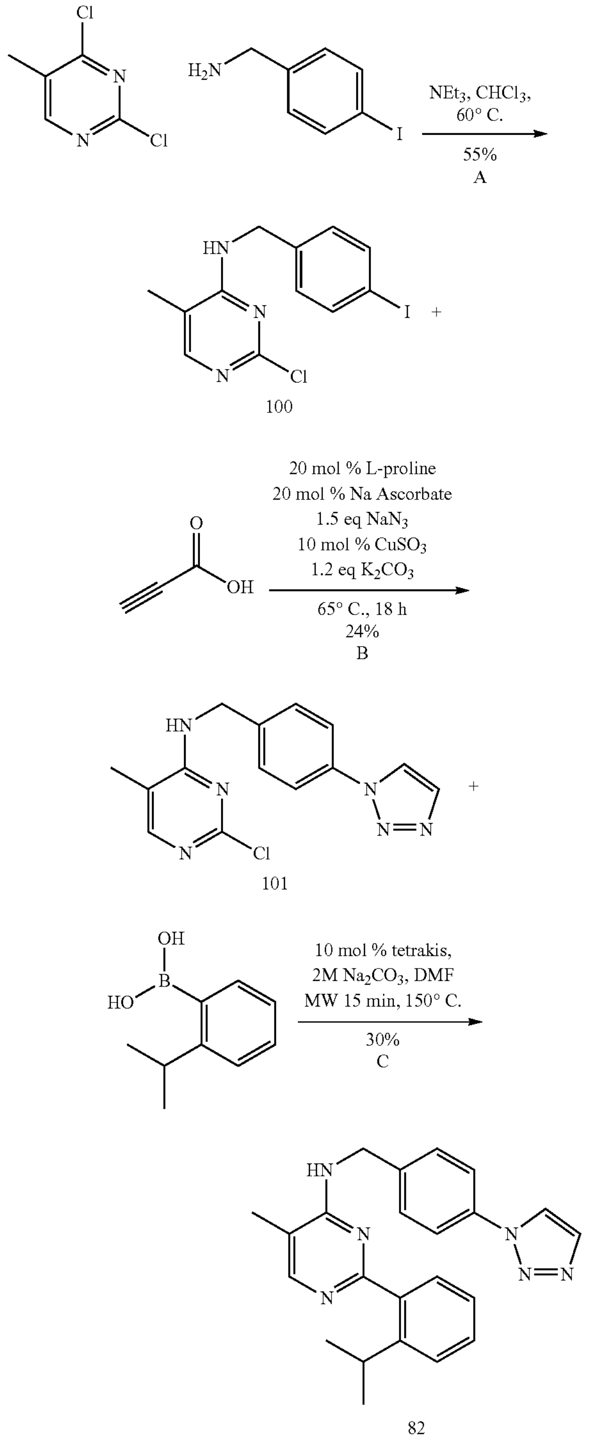

100

101

82

Another synthetic route to the inventive compounds involves amination of 2,4-dichloro-5-methylpyrimidine with 4-aminobenzylamine to give compound 102, arylation of 102 with 2-isopropylphenylboronic acid in the presence of silica-bound DPP-Pd and a base such as sodium carbonate in a solvent such as a mixture of DME/water under the influence of microwave irradiation to give compound 103, diazotization of the aryl amino group with t-butyl nitrite and TMS-azide to give 104, and then reaction of the azido moiety with TMS-acetylene in the presence of cupric sulfate in a solvent such as methanol/water, followed by treatment with TFA, to give compound 82.

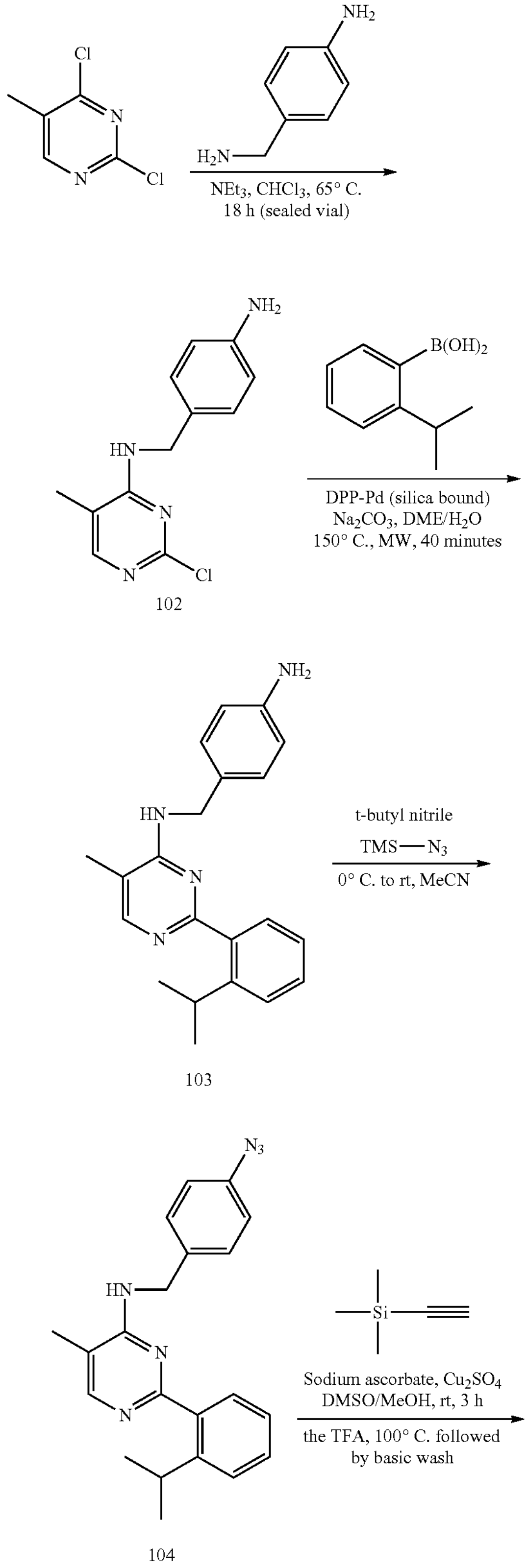

102

103

104

-continued

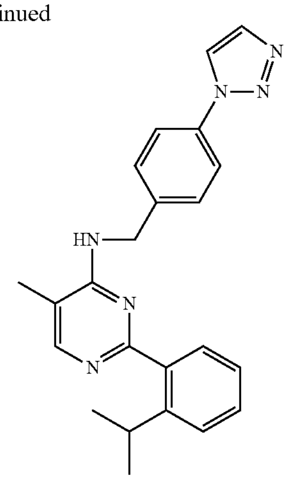

82

Another synthetic route to the inventive compounds involves conversion of 4-cyanoaniline 105 to the triazolylbenzylamine 106 via (a) conversion to the corresponding azide using t-butyl nitrite followed by treatment with azidotrimethylsilane, (b) reaction of the azide with ethynyltrimethylsilane in the presence of cupric sulfate, (c) treatment with trifluoroacetic acid, and (d) catalytic reduction of the cyano group to provide 106. Compound 106 is reacted with 2,4-dichloro-5-methylpyrimidine in the presence of a base such as triethylamine in a solvent such as DMF to provide 107. Reaction of 107 with (2-isopropylphenyl)boronic acid in the presence of a base such as sodium carbonate, a catalyst such as DPP-Pd silica bound Silicycle™ in a solvent such as DME to provide compound 82.

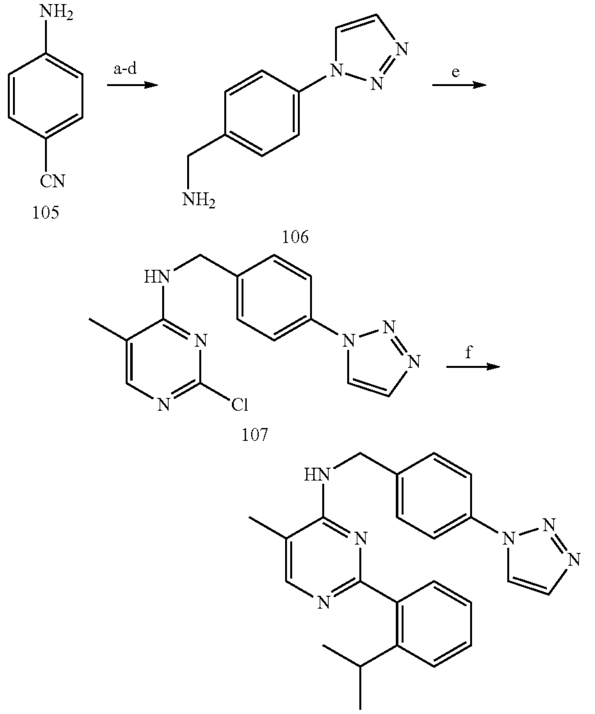

105 106 107 81

(a) TFA (1.0 equiv), rt, 5 min t-butyl nitrite (1.5 equiv), azidotrimethylsilane (1.4 equiv), 0° C., 30 min. (98%) (b) ethynyltrimethylsilane (6.0 equiv), sodium ascorbate (0.8 equiv), $Cu(II)SO_4$ (0.07 equiv), DMSO/$H_2O$, 80° C. 24 h (c) TFA (1 equiv), acetonitrile, reflux, 2 h, (57%). (d) H-Cube Pro®, 70 mm 10% Pd/C Catcart, 50° C., 40 bar, TFA, MeOH/DMF (10/1), (98%) (e) 2,4-dichloro-5-methylpyrimidine $NEt_3$ (3.0 equiv), DMF, 100° C., 18 h. (f) (2-isopropylphenyl)boronic acid (3.0 equiv), 2 M $Na_2CO3$ (4.0 equiv), DPP-Pd silica bound Silicycle® 0.26 mmol/g (19 mol %), DME, MW, 150° C., 30 min, 35-50% yield.

The synthesis of deuterated analogs of compounds of the invention can be performed as illustrated for an embodiment of the invention. Deuteration of 2-bromoacetophenone 105 with $D_2O$ gives the deuterated compound 106. Addition of $CD_3MgBr$ to the carbonyl group gives compound 107, which upon reduction with $Et_3SD$ in the presence of d-TFA in a solvent such as dichloromethane gives heptadeuterated 108. Formation of the boronic acid 109 followed by previously described steps gives the deuterated analog of 82, 110.

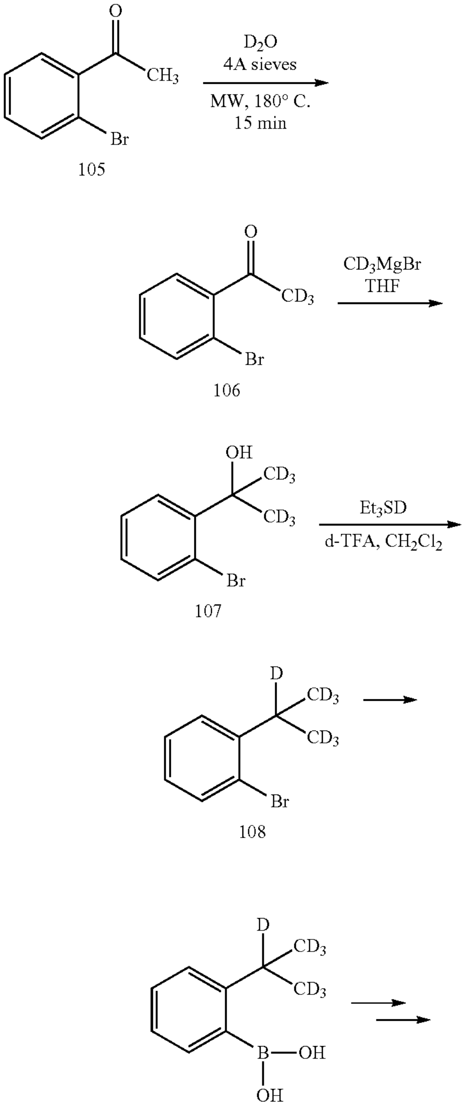

105 106 107 108 109

-continued

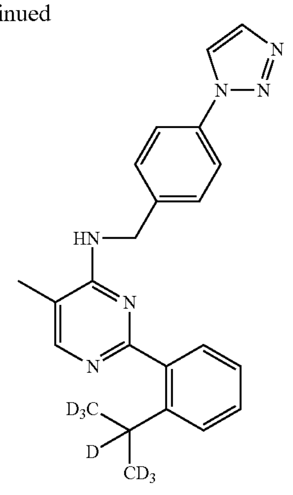

110

The present invention further provides a pharmaceutical composition comprising a pharmaceutically acceptable carrier and at least one compound or salt described herein.

It is preferred that the pharmaceutically acceptable carrier be one that is chemically inert to the active compounds and one that has no detrimental side effects or toxicity under the conditions of use.

The choice of carrier will be determined in part by the particular compound of the present invention chosen, as well as by the particular method used to administer the composition. Accordingly, there is a wide variety of suitable formulations of the pharmaceutical composition of the present invention. The following formulations for oral, aerosol, nasal, pulmonary, parenteral, subcutaneous, intravenous, intramuscular, intraperitoneal, intrathecal, intratumoral, topical, rectal, and vaginal administration are merely exemplary and are in no way limiting.

The pharmaceutical composition can be administered parenterally, e.g., intravenously, subcutaneously, intradermally, or intramuscularly. Thus, the invention provides compositions for parenteral administration that comprise a solution or suspension of the inventive compound or salt dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, e.g., Banker and Chalmers, eds., *Pharmaceutics and Pharmacy Practice*, J. B. Lippincott Company, Philadelphia, pp. 238-250 (1982), and Toissel, *ASHP Handbook on Injectable Drugs*, 4th ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound or salt of the present invention may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscannellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compound or salt of the present invention, alone or in combination with other suitable components, can be made into aerosol formulations to be administered via inhalation. The compounds are preferably supplied in finely divided form along with a surfactant and propellant. Typical percentages of active compound are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compound or salt of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

It will be appreciated by one of ordinary skill in the art that, in addition to the aforedescribed pharmaceutical compositions, the compound or salt of the present invention may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the inventive compound. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive compound or salt thereof, can be directed to the site of a specific tissue type, hepatic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.*, 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present invention may be administered intravenously, locally, topically, etc. in a dose that varies according to the mode of administration, the agent being delivered, and the stage of disease being treated.

In accordance with an embodiment, the invention provides a method of inhibiting a heterodimeric deubiquitinase complex in a cell. which method comprises administering to the cell an effective amount of a compound of the invention. In accordance with a certain embodiment, the heterodimeric deubiquitinase complex is USP1/UAF1. The cell can be present in a host, for example, the cell can be present in an animal.

Desirably, the compound or salt of the invention exhibits selectivity for USP1/UAF1 versus USP2, USPS, USP7, USPS, and USP12/46.

Preferably, the animal is a mammal. More preferably, the mammal is a human.

The term "mammal" includes, but is not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human. Furthermore, the subject can be the unborn offspring of any of the forgoing hosts, especially mammals (e.g., humans), in which case any screening of the subject or cells of the subject, or administration of compounds to the subject or cells of the subject, can be performed in utero.

In accordance with an embodiment, the invention provides a method of enhancing the chemotherapeutic treatment of cancer in a mammal undergoing treatment with an anti-cancer agent, which method comprises co-administering to the mammal an effective amount of a compound of the invention. In certain embodiments, the anti-cancer agent is a DNA damaging agent. The DNA damaging agent can be any suitable DNA damaging agent. Non-limiting examples of suitable DNA damaging agents include DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide. In a preferred embodiment, the DNA damaging agent is cisplatin. The DNA damaging agent can also be radiation or a biotherapeutic agent such as antibody.

The anticancer agent can also be chosen from reversible DNA binders, DNA alkylators, DNA strand breakers, and disruptors of DNA replication.

Examples of suitable reversible DNA binders include topetecan hydrochloride, irinotecan (CPT11-Camptosar), rubitecan, exatecan, nalidixic acid, TAS-103, etoposide, acridines (e.g., amsacrine, aminocrine), actinomycins (e.g., actinomycin D), anthracyclines (e.g., doxorubicin, daunorubicin), benzophenainse, XR 11576/MLN 576, benzopyridoindoles, Mitoxantrone, AQ4, Etopside, Teniposide, epipodophyllotoxins, and bisintercalating agents such as triostin A and echinomycin.

Examples of suitable DNA alkylators include sulfur mustard, the nitrogen mustards (e.g., mechlorethamine), chlorambucil, melphalan, ethyleneimines (e.g., triethylenemelamine, carboquone, diaziquone), methyl methanesulfonate, busulfan, CC-1065, duocarmycins (e.g., duocarmycin A, duocarmycin SA), metabolically activated alkylating agents such as nitrosoureas (e.g., carmustine, lomustine, (2-chloroethyl)nitrosoureas), triazne antitumor drugs such as triazenoimidazole (e.g., dacarbazine), mitomycin C, leinamycin, and the like.

Examples of suitable DNA strand breakers include doxorubicin and daunorubicin (which are also reversible DNA binders), other anthracyclines, bleomycins, tirapazamine, enediyne antitumor antibiotics such as neocarzinostatin, esperamicins, calicheamicins, dynemicin A, hedarcidin, C-1027, N1999A2, esperamicins, zinostatin, and the like.

An example of a disruptor of DNA replication is 5-fluorodeoxyuridine, also known as floxuridine. 5-Fluorodeoxyuridine is an FDA-approved drug for the treatment of hepatic colon metastases and is known to have activity in multiple cancers, including ovarian cancer. See, e.g., Power D G et al., *Mol Cancer Ther* 2009; 8:1015-25; Ardalan B, et al., J *Cancer Res Clin Oncol* 2004; 130:561-6; Vokes E E, et al., *Cancer Chemother Pharmacol* 1991; 28:69-73; Damascelli B et al., *Cancer* 1991; 68:995-8; Leichman L et al., *J Clin Oncol* 1992; 10:1933-42; Newman E et al., *Semin Oncol* 2005; 32:S97-100; Muggia F M et al., *Gynecol Oncol* 1996; 61:395-402; Brenner B et al., *Ann Oncol* 2006; 17:1404-11; Israel V K et al., *Cancer Chemother Pharmacol* 1995; 37:32-8; Muggia F M et al., *Chemother Pharmacol* 1991; 28:241-50.

In certain embodiments, the DNA damaging agent can be radiation, such as radiation that induces a DNA cross-linking in a cell when applied to the cell. DNA cross-linking radiation includes ionizing radiation and ultraviolet (UV) radiation. Ionizing radiation consist of subatomic particles or electromagnetic waves that are sufficiently energetic to cause ionization by detaching electrons from atoms or molecules. Ionization depends on the energy of the impinging individual particles or waves. In general, ionizing particles or photons with energies above a few electron volts can be ionizing. Non-limiting examples of ionizing particles are alpha particles, beta particles, and neutrons. The ability of photons to ionize a atom or molecule depends on its frequency. Short-wavelength radiation such as high frequency ultraviolet, x-rays, and gamma rays, is ionizing. Ionizing radiation comes from radioactive materials, x-ray tubes, and particle accelerators.

In certain embodiments, the anticancer or DNA damaging agent can be a biotherapeutic. Non-limiting examples of suitable biotherapeutics include rInterferon-$\alpha_{2a}$, rInterferon-$\alpha_{2b}$, rinterleukin-2, rG-CSF, rGM-CSF, and rErythropoietin.

In certain embodiments, the anticancer agent can be an antibody, such as a monoclonal antibody. Non-limiting examples of suitable therapeutic monoclonal antibodies for use in the present invention include trastuzumab, an anti-ErbB2/HER2 for breast cancer, cetuximab, an anti-ErbB1/EGFR for colorectal cancer, and bevacizumab, an anti-VEGF for colorectal, breast and lung cancers (G. Adams et al., *Nature Biotechnology* 23: 1147-57 (2005)). Multitarget inhibitors, such as Sutent which inhibits TK activity of VEGFR, PDGFR and FGFR, are also suitable for use in the inventive method.

In certain embodiments, the anticancer agent can be a proteasome inhibitor, such as bortezomib.

In accordance with an embodiment, the invention provides a method of treating cancer in a mammal in need thereof, comprising administering to the animal a compound or salt of the invention. In accordance with these embodiments, the compound or salt of the invention is administered to the mammal by itself, i.e., without co-administration of an anticancer agent, radiation, or biotherapeutic agent. In some embodiments, the compound or salt of the invention can be administered concomitantly with radiation and/or biotherapeutic agent.

The cancer can be any suitable cancer. For example, the cancer may be adrenocortical carcinoma, AIDS-related lymphoma, AIDS-related malignancies, anal cancer, cerebellar astrocytoma, extrahepatic bile duct cancer, bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, liver cancer, non-small cell lung cancer, small cell lung cancer, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (e.g. renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodermal and pineal tumors, cutaneous t-cell lymphoma, testicular cancer, malignant thymoma, thyroid cancer, gestational trophoblastic tumor, urethral cancer, uterine sarcoma, vaginal cancer, vulvar cancer, and Wilms' tumor. In a preferred embodiment, the cancer is a non-small cell lung cancer.

In any of the embodiments of the invention, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. Treatment of cancer can be evidenced, for example, by a reduction in tumor size, a reduction in tumor burden, a reduction in clinical symptoms resulting from the cancer, or other parameters well known in the art that are specific to the cancer. The phrase "treating a disease" refers to inhibiting the full development of a disease or condition, for example, in a subject who is at risk for a disease such as cancer, particularly a metastatic cancer.

By the term "coadminister" is meant that each of the at least two compounds be administered during a time frame wherein the respective periods of biological activity overlap. Thus, the term includes sequential as well as coextensive administration of two or more drug compounds. The compounds can be administered simultaneously, separately (chronologically staggered), cyclically, or sequentially and in any order, e.g., before or after.

One skilled in the art will appreciate that suitable methods of utilizing a compound and administering it to a human for the treatment or prevention of disease states, in particular, cancer, which would be useful in the method of the present invention, are available. Although more than one route can be used to administer a particular compound, a particular route can provide a more immediate and more effective reaction than another route. Accordingly, the described methods are merely exemplary and are in no way limiting.

The dose administered to a mammal, particularly, a human, in accordance with the present invention should be sufficient to effect the desired response. Such responses include reversal or prevention of the bad effects of the disease for which treatment is desired or to elicit the desired benefit. One skilled in the art will recognize that dosage will depend upon a variety of factors, including the age, condition, and body weight of the human, as well as the source, particular type of the disease, and extent of the disease in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg of one or more of the compounds described above per kg body weight of the mammal.

The therapeutically effective amount of the compound or compounds administered can vary depending upon the desired effects and the factors noted above. Typically, dosages will be between 0.01 mg/kg and 250 mg/kg of the subject's body weight, and more typically between about 0.05 mg/kg and 100 mg/kg, such as from about 0.2 to about 80 mg/kg, from about 5 to about 40 mg/kg or from about 10 to about 30 mg/kg of the subject's body weight. Thus, unit dosage forms can be formulated based upon the suitable ranges recited above and the subject's body weight. The term "unit dosage form" as used herein refers to a physically discrete unit of therapeutic agent appropriate for the subject to be treated.

Alternatively, dosages are calculated based on body surface area and from about 1 $mg/m^2$ to about 200 $mg/m^2$, such as from about 5 $mg/m^2$ to about 100 $mg/m^2$ will be administered to the subject per day. In particular embodiments, administration of the therapeutically effective amount of the compound or compounds involves administering to the subject from about 5 $mg/m^2$ to about 50 $mg/m^2$, such as from about 10 $mg/m^2$ to about 40 $mg/m^2$ per day. It is currently believed that a single dosage of the compound or compounds is suitable, however a therapeutically effective dosage can be supplied over an extended period of time or in multiple doses per day. Thus, unit dosage forms also can be calculated using a subject's body surface area based on the suitable ranges recited above and the desired dosing schedule.

The following examples further illustrate the invention but, of course, should not be construed as in any way limiting its scope.

General Methods for Chemistry.

All air or moisture sensitive reactions were performed under positive pressure of nitrogen with oven-dried glassware. Anhydrous solvents such as dichloromethane, N,N-dimethylformamide (DMF), acetonitrile, methanol and triethylamine were purchased from Sigma-Aldrich. Preparative purification was performed on a Waters semi-preparative HPLC system. The column used was a Phenomenex Luna C18 (5 micron, 30×75 mm) at a flow rate of 45 mL/min. The mobile phase consisted of acetonitrile and water (each containing 0.1% trifluoroacetic acid). A gradient of 10% to 50% acetonitrile over 8 minutes was used during the purification. Fraction collection was triggered by UV detection (220 nm). Analytical analysis was performed on an Agilent LC/MS (Agilent Technologies, Santa Clara, Calif.). Method 1: A 7 minute gradient of 4% to 100% Acetonitrile (containing 0.025% trifluoroacetic acid) in water (containing 0.05% trifluoroacetic acid) was used with an 8 minute run time at a flow rate of 1 mL/min. A Phenomenex Luna C18 column (3 micron, 3×75 mm) was used at a temperature of 50° C. Method 2: A 3 minute gradient of 4% to 100% Acetonitrile (containing 0.025% trifluoroacetic acid) in water (containing 0.05% trifluoroacetic acid) was used with a 4.5 minute run time at a flow rate of 1 mL/min. A Phenomenex Gemini Phenyl column (3 micron, 3×100 mm) was used at a temperature of 50° C. Purity determination was performed using an Agilent Diode Array Detector for both Method 1 and Method 2. Mass determination was performed using an Agilent 6130 mass spectrometer with electrospray ionization in the positive mode. 1H NMR spectra were recorded on Varian 400 MHz spectrometers. Chemical shifts are reported in ppm with undeuterated solvent (DMSO-d6 at 2.49 ppm) as internal standard for DMSO-d6 solutions. All of the analogs tested in the biological assays have purity greater than 95%, based on both analytical methods. High resolution mass spectrometry was recorded on Agilent 6210 Time-of-Flight LC/MS system. Confirmation of molecular formula was accomplished using electrospray ionization in the positive mode with the Agilent Masshunter software (version B.02).

Cell Lines and Culture Conditions

The H596 [human non-small cell lung cancer (NSCLC)] cell line was cultured in RFMI-1640 medium containing 10% fetal bovine serum (FBS) at 37° C. and 5% $CO_2$. The HEK293T (human embryonic kidney 293T), U2OS (human osteosarcoma), and HCT116 (human colon cancer) cell lines were cultured in Dulbecco's modified Eagle's medium (DMEM) supplemented with 10% FBS at 37° C. and 5% $CO_2$. All culture mediums contain 100 units/mL penicillin and 0.1 mg/mL streptomycin as antibiotics.

Reagents and Antibodies Sources

Ubiquitin-rhodamine110, K63-linked diubiquitin, full length USP7 (HAUSP), USP5 (Isopeptidase T), USP8, and the catalytic domain of USP2 (a. a. 259-605) were purchased from Boston Biochem. USP1/UAF1 and USP46/UAF1 complexes were generated as previously described (Chen, J., et al, *Chemistry and Biology*, 2011, 18(11): 1390-1400). Both human anti-PCNA and anti-FANCD2 antibodies were from Santa Cruz. USP1 antibody was from Abeam. HA-tag and HRP-conjugated anti-mouse antibodies were from Sigma-Aldrich. HRP-conjugated anti-rabbit secondary antibody was from Bio-Rad.

EXAMPLE 1

This example demonstrates a qHTS assay for USP1/UAF1 activity.

USP1/UAF1 activity was monitored in a fluorometric assay using ubiquitin-rhodamine110. Enzymatic reactions were conducted in an assay buffer (50 mM HEPES, pH 7.8, 0.5 mM EDTA, 100 mM NaCl, 1 mM TCEP, 0.1 mg/mL BSA, and 0.01% Tween-20) that contained 1 nM USP1/UAF1. Each individual compound was tested at five concentrations in the range of 0.46 to 115 µM. The plates were incubated for 15 min to attain equilibrium, and then the enzymatic reaction was initiated by dispensing 1 µL of Ub-Rho solution (150 nM final concentration). The plates were directly transferred to a ViewLux high-throughput CCD imager (PerkinElmer), where kinetic measurements of rhodamine fluorescence were acquired using a 480 nm excitation/540 nm emission filter set. The change in fluorescence intensity over a 5-minute reaction period (typically associated with less than 10% substrate conversion) was normalized against no-inhibitor and no-enzyme controls and the resulting percent inhibition data were fitted to a sigmoidal dose response using a four-parameter Hill equation. All screening operations were performed on a fully integrated robotic system (Kalypsys Inc., San Diego, Calif.) as described elsewhere. Plates containing DMSO only were included approximately every 50 plates throughout the screen to monitor any systematic trend in the assay signal associated with reagent dispenser variation or decrease in enzyme specific activity. PubChem AID: 651605. The assay protocol is set forth in Table 1.

TABLE 1

| Sequence | Parameter | Value | Description |
|---|---|---|---|
| 1 | Reagent | 3 µL | USP1/UAF1 (1 nM final conc.) or buffer-only control |
| 2a | Compound | 23 nL | Compound Library |
| 2b | Control | 23 nL | GW7647 |
| 3 | Time | 15 min | RT Incubation |
| 4 | Reagent | 1 µL | Ub-Rho Substrate (150 nM final conc.) |
| 5 | Detector | Fluorescence | ViewLux (Rhodamine optics) |
| 6 | Time | 5 min | RT Incubation |
| 7 | Detector | Fluorescence | ViewLux (Rhodamine optics) |

EXAMPLE 2

This example demonstrates a K63-linked diubiquitin gel assay.

Inhibitors at varied concentrations were added to the assay containing USP at an appropriate concentration (150 nM USP1/UAF1, 30 nM USP2, 15 nM USP5, 7.5 nM USP7, 255 nM USP8, and 600 nM USP46/UAF1) and 3 µM K63-linked diubiquitin in a buffer containing 50 mM HEPES (pH 7.8), 0.1 mg/mL BSA, 0.5 mM EDTA and 1 mM DTT. After 1 hour at 37° C., the reaction was quenched by the addition of Laemmli sample buffer. The reaction products were then separated on a 20% denaturing SDS-PAGE gel and stained with Coomassie Blue. The intensity of the individual diubiquitin and monoubiquitin bands were quantified using Quantity One software (Bio-Rad). The enzyme activity was normalized against no-inhibitor control and plotted against inhibitor concentration. The IC50 value was determined by fitting the dose response curve to the equation below using GraphPad Prism (GraphPad Software), $$Y = Y_0 + \frac{Y_{max} - Y_0}{1 + 10^{X - Log\,IC_{50}}}$$

where X=Log [inhibitor]; Y is the enzyme activity in percent relative to control. PubChem AID: 651621 (USP1/UAF1), 651622 (USP46/UAF1), 651623 (USP8), 651624 (USP7), 651625 (USP5), and 651626 (USP2).

EXAMPLE 3

This example demonstrates determination of Ki using diubiquitin gel assay.

The inhibition assay solution contained 150 nM USP1/UAF1, 7-80 μM K63-linked diubiquitin, and ML323 at varied concentrations in a buffer containing 50 mM HEPES, pH 7.8, 0.1 mg/mL BSA, 0.5 mM EDTA, and 1 mM DTT. The reaction was incubated for 10-90 minutes at 37° C., and then quenched by the addition of Laemmli sample buffer at the given time point. The reaction products were separated on a 20% denaturing SDS-PAGE gel and stained with Coomassie Blue. The intensity of the individual diubiquitin and monoubiquitin bands were quantified using Quantity One 4.3.1 (Biorad, Hercules, Calif.). The percentage of the conversion was determined and used to calculate the reaction rate. The Lineweaver-Burk plot was obtained by plotting 1/v against 1/[di-Ub] at four different inhibitor concentrations. For noncompetitive inhibition, Ki was determined by fitting the data to the equations shown below using Origin 8 (OriginLab Corp., Northampton, Mass.).

$$\frac{1}{v} = \left[\frac{K_m}{V_{max}}\left(\frac{1}{[S]}\right) + \frac{1}{V_{max}}\right]\left(1 + \frac{[I]}{K_i}\right)$$

$$\text{Slope} = \frac{K_m}{V_{max}}\left(1 + \frac{[I]}{K_i}\right)$$

$$\text{Intercept} = \frac{1}{V_{max}}\left(1 + \frac{[I]}{K_i}\right)$$

EXAMPLE 4

This example demonstrates reversible inhibition of USP1/UAF1 by an embodiment of the invention.

Figure 1:
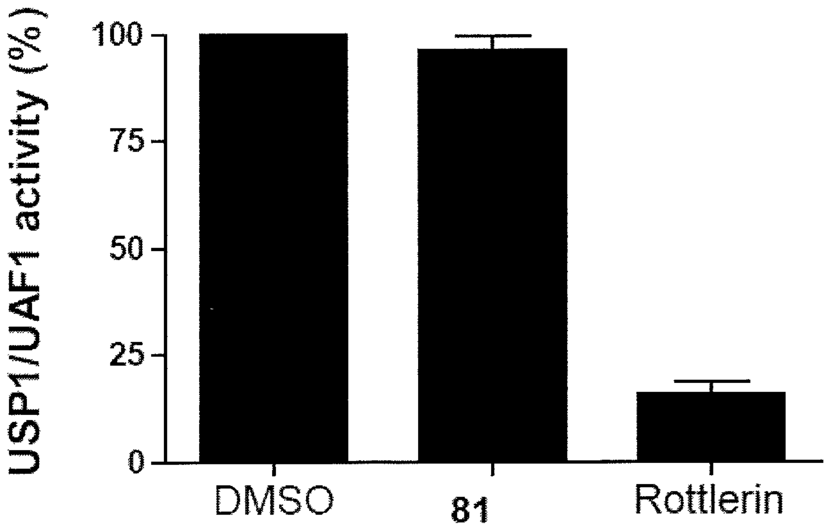
FIG. 1 illustrates reversible inhibition of USP1/UAF1 by an embodiment of the invention.
Figure 2A:
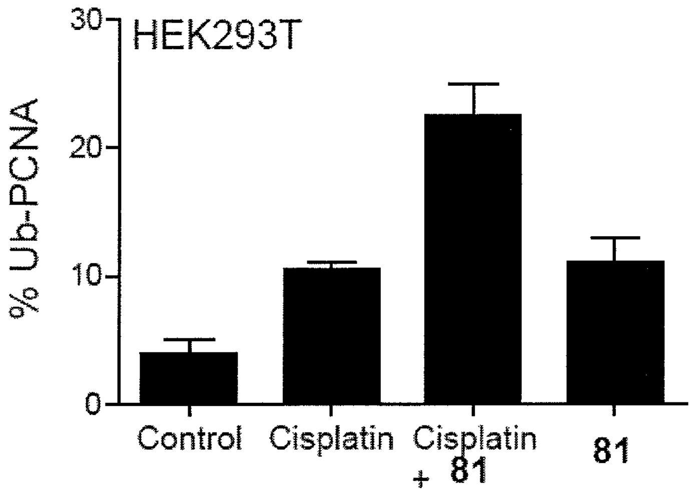
FIGS. 2A and 2B illustrate the increase in PCNA and FANCD2 monoubiquitination in HEK293T cells in accordance with an embodiment of the invention.
Figure 2B:
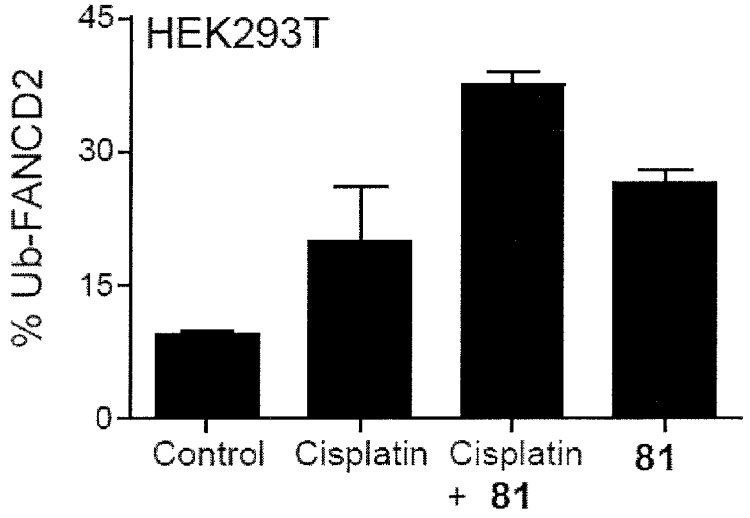
Figure 2C:
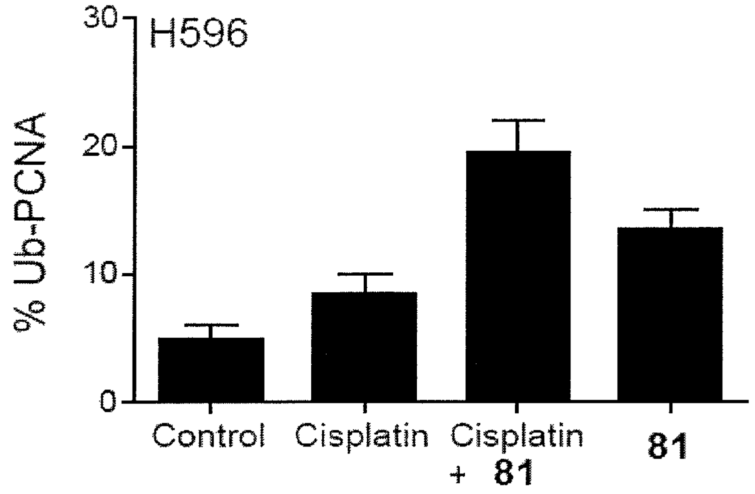
FIGS. 2C and 2D illustrate the increase in PCNA and FANCD2 monoubiquitination in H596 cells in accordance with an embodiment of the invention.
Figure 2D:
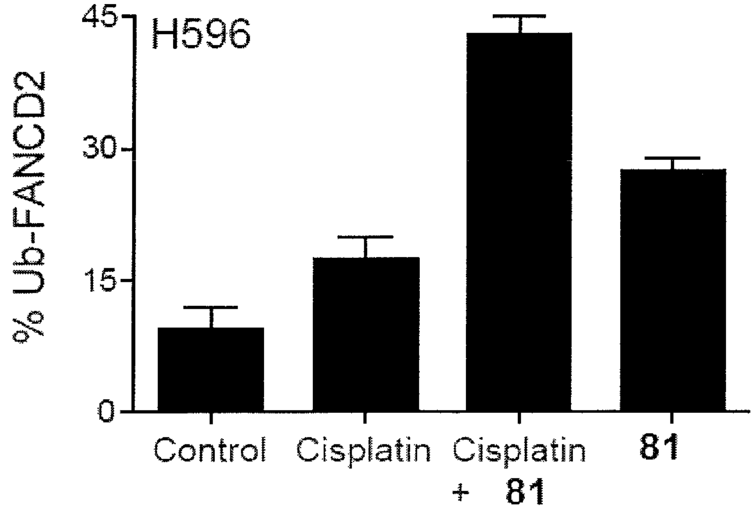

The compound (81) at a concentration of ten times its 1050 value was pre-incubated with 10 μM USP1/UAF1 at room temperature for 15 min. This solution was then diluted by 100-fold in assay buffer containing 50 mM HEPES, pH 7.8, 0.1 mg/mL BSA, 0.5 mM EDTA, and 1 mM DTT and incubated at room temperature for an additional 15 min. Next, 20 μM K63-linked diubiquitin was added into the solution and incubated at 37° C. for 10 min. Laemmli sample buffer was added to quench the reaction. The reaction products were then separated on a 20% denaturing SDS-PAGE gel and stained with Coomassie Blue. USP1/UAF1 incubated with DMSO was treated as 100% USP1/UAF1 activity. Rottlerin was utilized as an irreversible control inhibitor. The results are illustrated in FIG. 1.

EXAMPLE 5

This example demonstrates inhibition of the cellular activity of USP1/UAF1 by an embodiment of the invention.

HEK293T or H596 cells were plated in 10 cm dishes and synchronized in S-phase with the double-thymidine block method as described previously (Chen et al., Chemistry & Biology, 2011. 18(11): 1390-400). Then cells were treated with 100 μM cisplatin, 30 μM compound 81, or 100 μM cisplatin plus 30 μM compound 81. Negative control cells were treated with an equal volume of DMSO and saline (0.9% NaCl). After 6 hr at 37° C., cells were harvested and lysed. Cell extracts were separated on SDS-PAGE and transferred to nitrocellulose membrane. The membranes were then blotted with PCNA antibody or FANCD2 antibody, followed by incubation with HRP-conjugated anti-mouse secondary antibody. Images were quantified in FluorChem Q software (Imgen Technologies).

Alternatively, HCT116 cells were plated in 6-well plates and allowed to adhere overnight. Cells were treated with the indicated concentrations of compound 81 and were incubated for an additional 6 hr. Western blot analysis using anti-PCNA antibody was performed as described above. The results are illustrated in FIG. 2.

As is apparent from the results illustrated in FIG. 2, treatment of HEK293T and H596 cells with compound 81 leads to an increase in PCNA and FANCD2 monoubiquitination as compared to control. Treatment of HEK293T and H596 cells with compound 81 and with cisplatin leads to an increase in PCNA and FANCD2 monoubiquitination as compared to treatment with control, compound 81 alone, or cisplatin alone.

EXAMPLE 6

This example demonstrates cytotoxicity and clonogenicity assays for an embodiment of the invention.

For cytotoxicity assays, $5\times10^3$ H596 cells were seeded in each well of the 96-well plate and grown for 24 hr in humidified incubator. Cells were initially treated with cisplatin or compound 81 individually for 48 hr to determine the EC50 of each compound. In the combination assay, cisplatin was dissolved in saline solution and compound 81 was dissolved in DMSO. Equal volume of above solutions was added to each well and cells were incubated for 48 hr. Cells treated with equal volume of DMSO and saline were used as control and designated as 100% viability. The cell viability was measured by CCK-8 solution (Dojindo Molecular Technologies, Inc) as previously described (Chen, J., et al.).

For the colony formation assay, H596 cells were seeded at the density of 200 cells per well in 6-well plates and grown overnight in humidified incubator. The medium was replaced with growth medium containing cisplatin and compound 81 at different concentrations individually or in combination. After 48 hr treatment, the medium was replaced with fresh growth medium and the plates were incubated for an additional 7-8 days to allow for colony formation. Cells were then fixed with methanol and stained with 0.1% crystal violet (Sigma-Aldrich). The number of colonies consisting of 50 or more cells was scored. Cells treated with equal volume of DMSO and saline were used as a control and designated as 100%. Colony numbers were determined from triplicate plates. Dose-response curves for cytotoxicity and colony formation assays were generated by using GraphPad Prism and analyzed using CalcuSyn (Biosoft) to calculate the combination index (CI), which was determined for the fraction of cells affected McGovern, S. L., et al., J. Med. Chem. 2003, 46(20): 4265-4272) following addition of the fixed ratios of cisplatin and compound 81.

The results are illustrated in FIGS. 3A-3D. FIGS. 3A and 3C show the cytotoxicity and effect on colony number, respectively, with cisplatin alone as a diamond, compound 81 as a triangle, cisplatin plus compound 81 at a 1:1 ratio as a circle, and cisplatin plus compound 81 at a 1:4 ratio as a square. FIGS. 3B and 3D show the combination index analysis on cytotoxicity and effect on colony number, respectively with ratios of cisplatin and compound 81 of 1:1 as triangles and ratios of 1:4 as circles. The dashed horizontal lines represent a combination index=1. Cisplatin alone killed H596 cells at an $EC_{50}$ of 486 nM, while compound 81 killed H596 cells at an EC50 of >10 μM. The combination of cisplatin and compound 81 at ratios of 1:1 and 1:4 killed H596 cells at $EC_{50}$ values of 171 nM and 59 nM, respectively.

EXAMPLE 7

This example demonstrates a synthesis of an embodiment of the invention.

Step A: 2,4-dichloro-5-methylpyrimidine (0.300 g, 1.84 mmol) and 4-iodobenzylamine, HCl (0.496 g, 1.84 mmol) were dissolved in chloroform (4 mL). Triethylamine (0.770 mL, 3.00 mmol) was added and the sealed tube was heated at 60° C. overnight. The reaction was purified directly by flash column chromatography (gradient elution with 0→100% ethyl acetate/hexane) to yield pure 2-chloro-5-methyl-N-(4-iodobenzyl)pyrimidin-4-amine (0.365 g, 1.02 mmol, 55%).

Step B: The requisite phenyl iodide (0.100 g, 0.278 mmol) was combined in a sealed tube with L-proline (0.006 g, 0.056 mmol), sodium ascorbate (0.011 g, 0.056 mmol), $NaN_3$ (0.027 g, 0.417 mmol), $Cu(II)SO_4$ (0.004 g, 0.028 mmol), $K_2CO_3$ (0.046 g, 0.334 mmol), and propiolic acid (0.016 mL, 0.278 mmol) in DMSO (1.00 mL) and water (0.111 mL). The mixture was heated at 65° C. overnight. The resulting mixture was quenched with a saturated aq. $NH_4Cl$ solution (5 mL) and extracted with ethyl acetate (5 mL). The organic layer was washed with brine (5 mL), dried with $MgSO_4$, and concentrated in vacuo. The crude product was isolated by flash column chromatography (gradient elution with 0→100% ethyl acetate/hexane) to yield pure triazole (0.020 g, 0.067 mmol, 23%).

Step C: The methylpyrimidine triazole derivative (0.020 g, 0.067 mmol) was combined with 2-isopropylphenylboronic acid (0.013 g, 0.080 mmol), $Pd(PPh_3)_4$ (0.008 g, 0.007 mmol), and sodium carbonate (2 M in water, 0.067 mL, 0.133 mmol) in DMF (0.500 mL). The reaction was heated at 150° C. for 15 min in a Biotage Initiator® microwave reactor. The resulting mixture was filtered over Celite and purified by HPLC (gradient 20-100% acetonitrile w/0.1% TFA in water w/0.1% TFA) to yield, after lyophilization, pure N-(4-(1H-1,2,3-triazol-1-yl)benzyl)-5-methyl-2-(2-isopropylphenyl)pyrimidin-4-amine (81) as a TFA salt (0.010 g, 0.020 mmol, 30%).

EXAMPLE 8

This example illustrates the USP1/UAF1 inhibitory activity of several embodiments of the invention. Compounds were assayed as described in Example 1. The results are set forth in Table 1.

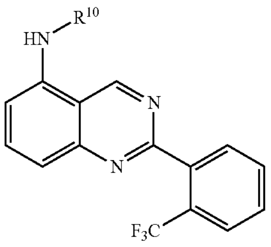

TABLE 1

| Compound | $R^{10}$ | IC50 (μM) |
|---|---|---|
| 1 | 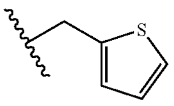 [SMILES: *Cc1cccs1] | 7.9 |
| 5 | 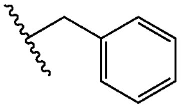 [SMILES: *Cc1ccccc1] | 2.4 |
| 6 | 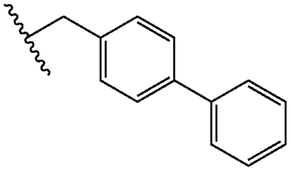 [SMILES: *Cc1ccc(-c2ccccc2)cc1] | 3.0 |
| 7 | 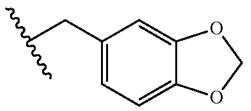 [SMILES: *Cc1ccc2c(c1)OCO2] | 5.4 |
| 8 | 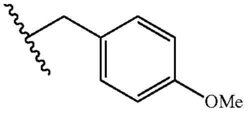 [SMILES: *Cc1ccc(OC)cc1] | 3.0 |
| 9 | 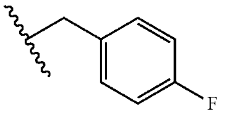 [SMILES: *Cc1ccc(F)cc1] | 2.4 |
| 10 | 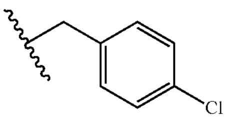 [SMILES: *Cc1ccc(Cl)cc1] | 3.0 |
| 11 | 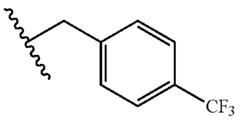 [SMILES: *Cc1ccc(C(F)(F)F)cc1] | 5.4 |
| 12 | 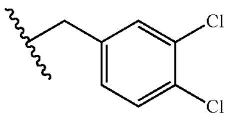 [SMILES: *Cc1ccc(Cl)c(Cl)c1] | 11 |
| 13 | 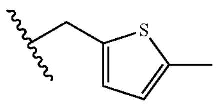 [SMILES: *Cc1ccc(C)s1] | 4.3 |
| 14 | 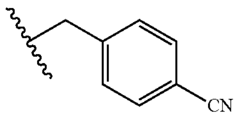 [SMILES: *Cc1ccc(C#N)cc1] | 3.4 |

TABLE 1-continued
| Compound | $R^{10}$ | IC50 (μM) |
|---|---|---|
| 15 | 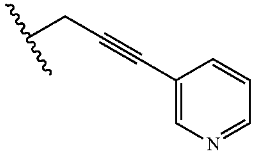 [SMILES: *CC#Cc1cccnc1] | 7.6 |
| 16 | 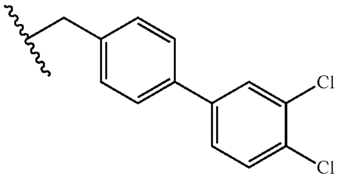 [SMILES: *Cc1ccc(-c2ccc(Cl)c(Cl)c2)cc1] | 1.4 |
| 17 | 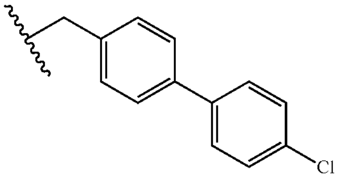 [SMILES: *Cc1ccc(-c2ccc(Cl)cc2)cc1] | 2.2 |
| 18 | 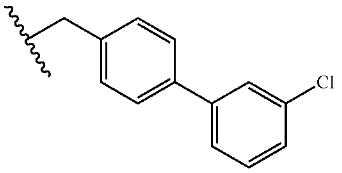 [SMILES: *Cc1ccc(-c2cccc(Cl)c2)cc1] | 1.7 |
| 19 | 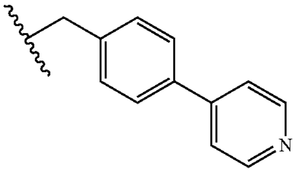 [SMILES: *Cc1ccc(-c2ccncc2)cc1] | 0.48 |
| 20 | 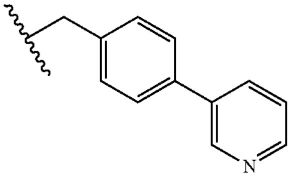 [SMILES: *Cc1ccc(-c2cccnc2)cc1] | 0.61 |
| 21 | 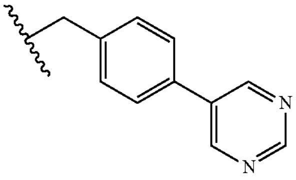 [SMILES: *Cc1ccc(-c2cncnc2)cc1] | 1.9 |
| 22 | 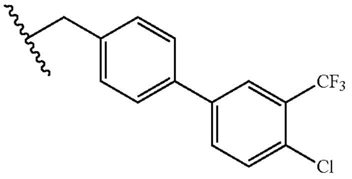 [SMILES: *Cc1ccc(-c2ccc(Cl)c(C(F)(F)F)c2)cc1] | 2.2 |
TABLE 1-continued
| Compound | $R^{10}$ | IC50 (μM) |
|---|---|---|
| 23 | 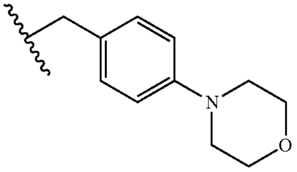 [SMILES: *Cc1ccc(N2CCOCC2)cc1] | 7.6 |
| 24 | 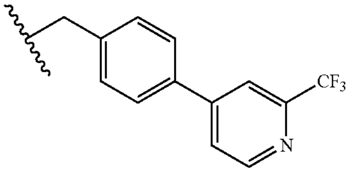 [SMILES: *Cc1ccc(-c2ccnc(C(F)(F)F)c2)cc1] | 4.3 |
| 25 | 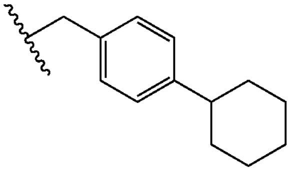 [SMILES: *Cc1ccc(C2CCCCC2)cc1] | 5.8 |
EXAMPLE 9
This example illustrates the USP1/UAF1 inhibitory activity of several embodiments of the invention. Compounds were assayed as described in Example 1. The results are set forth in Table 2.
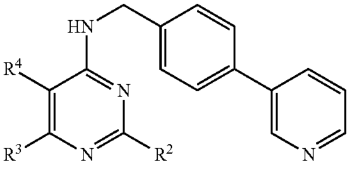
TABLE 2
| Compound | $R^2$ | $R^2$ | $R^4$ | $IC_{50}$ (μM) |
|---|---|---|---|---|
| 26 | 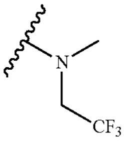 [SMILES: *N(C)CC(F)(F)F] | 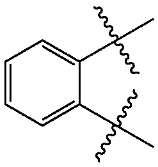 | | 7.6 |
| 27 | 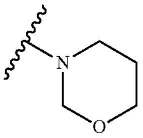 [SMILES: *N1CCCOC1] | 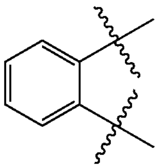 [SMILES: *c1ccccc1*] | | inactive |

TABLE 2-continued
| Compound | $R^2$ | $R^2$ | $R^4$ | $IC_{50}$ (μM) |
|---|---|---|---|---|
| 28 | 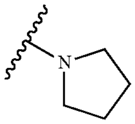 [SMILES: *N1CCCC1] | 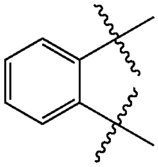 [SMILES: *c1ccccc1*] | | 27 |
| 29 | 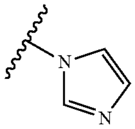 [SMILES: *n1ccnc1] | 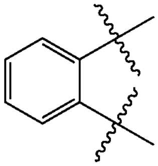 [SMILES: *c1ccccc1*] | | 27 |
| 30 | 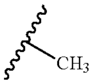 | 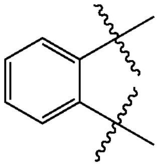 [SMILES: *c1ccccc1*] | | inactive |
| 31 | 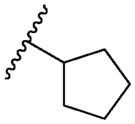 [SMILES: *C1CCCC1] | 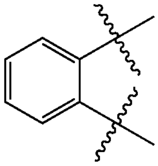 [SMILES: *c1ccccc1*] | | 17 |
| 32 | 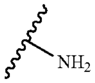 | 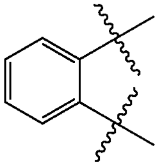 [SMILES: *c1ccccc1*] | | inactive |
| 33 | 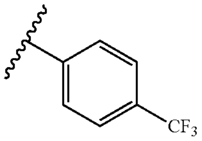 [SMILES: *c1ccc(C(F)(F)F)cc1] | 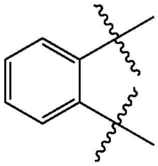 [SMILES: *c1ccccc1*] | | inactive |
| 34 | 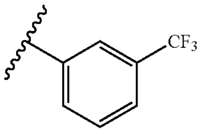 [SMILES: *c1cccc(C(F)(F)F)c1] | 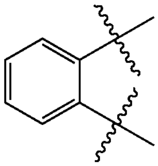 [SMILES: *c1ccccc1*] | | 27 |
| 35 | 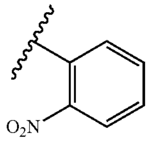 [SMILES: *c1ccccc1[N+](=O)[O-]] | 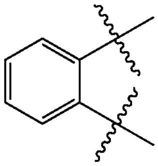 [SMILES: *c1ccccc1*] | | 4.3 |
TABLE 2-continued
| Compound | $R^2$ | $R^2$ | $R^4$ | $IC_{50}$ (μM) |
|---|---|---|---|---|
| 36 | 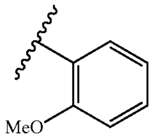 [SMILES: *c1ccccc1OC] | 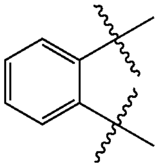 [SMILES: *c1ccccc1*] | | 0.68 |
| 37 | 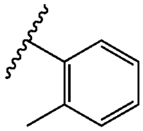 [SMILES: *c1ccccc1C] | 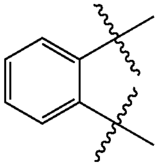 [SMILES: *c1ccccc1*] | | 0.48 |
| 38 | 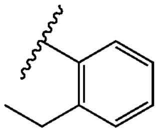 [SMILES: *c1ccccc1CC] | 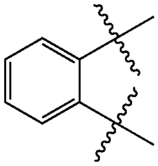 [SMILES: *c1ccccc1*] | | 0.61 |
| 39 | 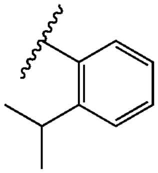 [SMILES: *c1ccccc1C(C)C] | 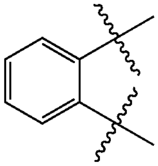 [SMILES: *c1ccccc1*] | | 0.15 |
| 40 | 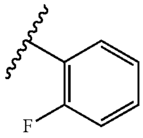 [SMILES: *c1ccccc1F] | 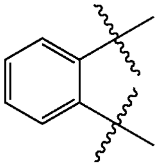 [SMILES: *c1ccccc1*] | | 3.4 |
| 41 | 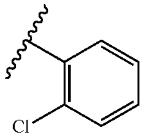 [SMILES: *c1ccccc1Cl] | 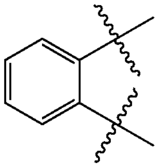 [SMILES: *c1ccccc1*] | | 0.86 |
| 42 | 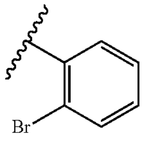 [SMILES: *c1ccccc1Br] | 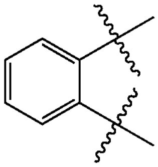 [SMILES: *c1ccccc1*] | | 0.96 |
| 43 | 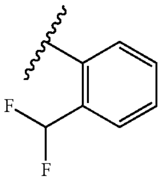 [SMILES: *c1ccccc1C(F)F] | 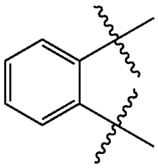 [SMILES: *c1ccccc1*] | | 1.4 |

TABLE 2-continued
| Compound | $R^2$ | $R^2$ | $R^4$ | $IC_{50}$ (µM) |
|---|---|---|---|---|
| 44 | 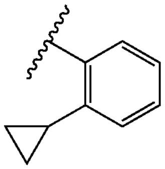 [SMILES: *c1ccccc1C1CC1] | $CH_3$ | H | 0.34 |
| 45 | 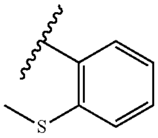 [SMILES: *c1ccccc1SC] | $CH_3$ | H | 0.34 |
| 46 | 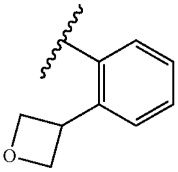 [SMILES: *c1ccccc1C1COC1] | $CH_3$ | H | inactive |
| 47 | 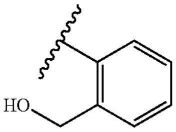 [SMILES: *c1ccccc1CO] | $CH_3$ | H | 8.6 |
| 48 | 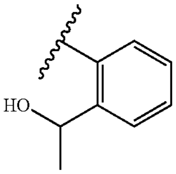 [SMILES: *c1ccccc1C(C)O] | $CH_3$ | H | 1.4 |
| 49 | 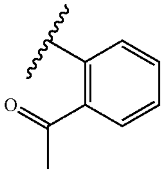 [SMILES: *c1ccccc1C(C)=O] | $CH_3$ | H | 12 |
EXAMPLE 10
This example illustrates the USP1/UAF1 inhibitory activity of several embodiments of the invention. Compounds were assayed as described in Example 1. The results are set forth in Table 3.
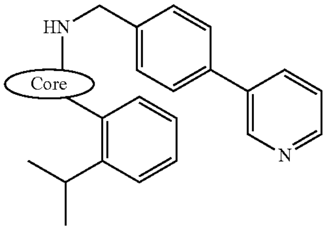
TABLE 3
| Compound | Core | $IC_{50}$ (µM) |
|---|---|---|
| 50 | 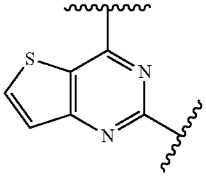 [SMILES: *c1nc(*)c2sccc2n1] | 0.12 |
| 51 | 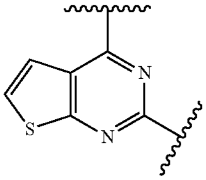 [SMILES: *c1nc(*)c2ccsc2n1] | 0.24 |
| 52 | 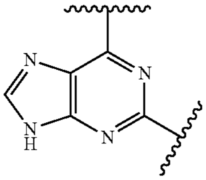 [SMILES: *c1nc(*)c2nc[nH]c2n1] | 2.12 |
| 53 | 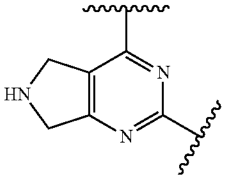 [SMILES: *c1nc(*)c2c(n1)CNC2] | 1.5 |
| 54 | 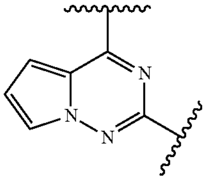 [SMILES: *c1nc(*)c2cccn2n1] | 0.22 |
| 55 | 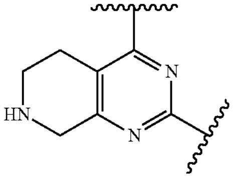 [SMILES: *c1nc(*)c2c(n1)CNCC2] | 0.48 |
| 56 | 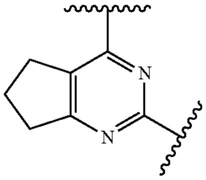 [SMILES: *c1nc(*)c2c(n1)CCC2] | 0.14 |
| 57 | 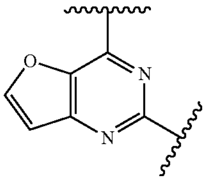 [SMILES: *c1nc(*)c2occc2n1] | 0.15 |

TABLE 3-continued
| Compound | Core | $IC_{50}$ (μM) |
|---|---|---|
| 58 | 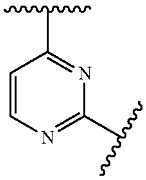 [SMILES: *c1ccnc(*)n1] | 0.12 |
| 59 | 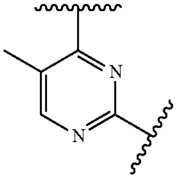 [SMILES: *c1ncc(C)c(*)n1] | 0.068 |
| 60 | 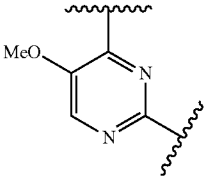 [SMILES: *c1ncc(OC)c(*)n1] | 0.043 |
| 61 | 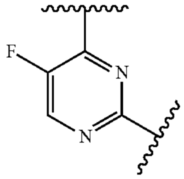 [SMILES: *c1ncc(F)c(*)n1] | 0.061 |
| 62 | 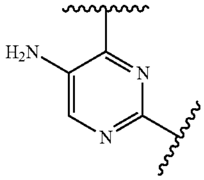 [SMILES: *c1ncc(N)c(*)n1] | 0.27 |
| 63 | 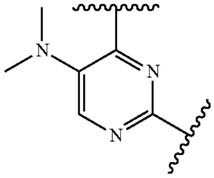 [SMILES: *c1ncc(N(C)C)c(*)n1] | 0.15 |
| 64 | 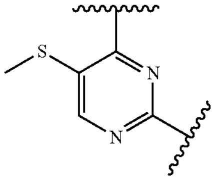 [SMILES: *c1ncc(SC)c(*)n1] | 0.086 |
| 65 | 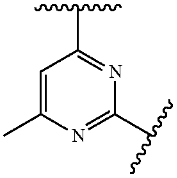 [SMILES: *c1cc(C)nc(*)n1] | 0.48 |
| 66 | 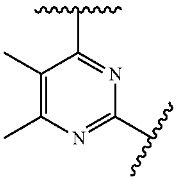 [SMILES: *c1nc(*)c(C)c(C)n1] | 0.14 |
EXAMPLE 11
This example illustrates the USP1/UAF1 inhibitory activity of several embodiments of the invention. Compounds were assayed as described in Example 1. The results are set forth in Table 4.
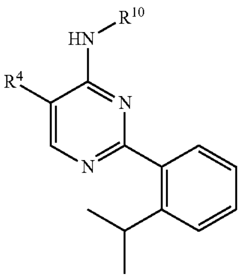
TABLE 4
| Compound | $R^{10}$ | $R^4$ | $IC_{50}$ (μM) |
|---|---|---|---|
| 67 | 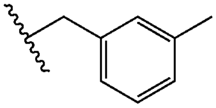 [SMILES: *Cc1cccc(C)c1] | Me | 0.14 |
| 68 | 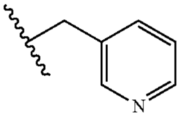 [SMILES: *Cc1cccnc1] | Me | 2.2 |
| 69 | 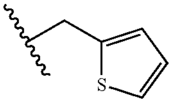 [SMILES: *Cc1cccs1] | Me | 0.22 |
| 70 | 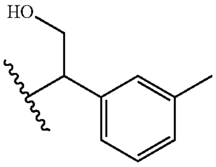 [SMILES: *C(CO)c1cccc(C)c1] | Me | 1.1 |
| 71 | 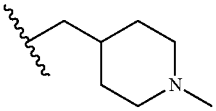 [SMILES: *CC1CCN(C)CC1] | Me | 30 |

TABLE 4-continued
| Compound | $R^{10}$ | $R^4$ | $IC_{50}$ (μM) |
|---|---|---|---|
| 72 | 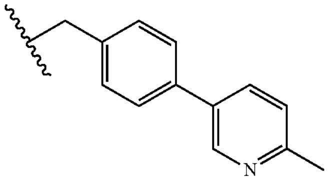 [SMILES: *Cc1ccc(-c2ccc(C)nc2)cc1] | Me | 0.043 |
| 73 | 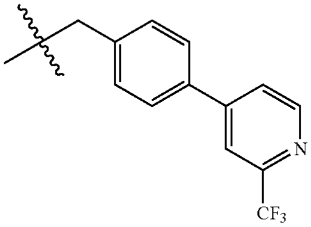 [SMILES: *Cc1ccc(-c2ccnc(C(F)(F)F)c2)cc1] | Me | 0.38 |
| 74 | 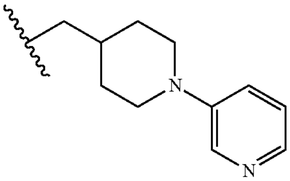 [SMILES: *CC1CCN(c2cccnc2)CC1] | Me | 0.048 |
| 75 | 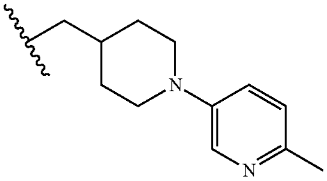 [SMILES: *CC1CCN(c2ccc(C)nc2)CC1] | Me | 2.2 |
| 76 | 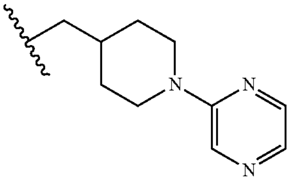 [SMILES: *CC1CCN(c2cnccn2)CC1] | Me | 0.12 |
| 77 | 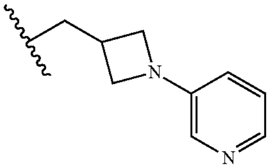 [SMILES: *CC1CN(c2cccnc2)C1] | Me | 6.8 |
| 78 | 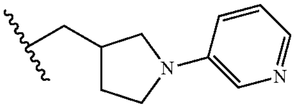 [SMILES: *CC1CCN(c2cccnc2)C1] | Me | 0.48 |
| 79 | 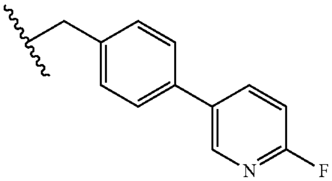 [SMILES: *Cc1ccc(-c2ccc(F)nc2)cc1] | Me | 0.061 |
| 80 | 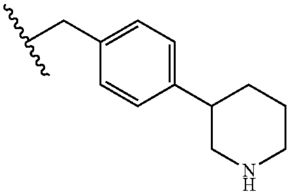 [SMILES: *Cc1ccc(C2CCCNC2)cc1] | Me | 7.6 |
| 81 | 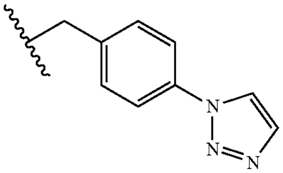 [SMILES: *Cc1ccc(-n2ccnn2)cc1] | Me | 0.076 |
| 82 | 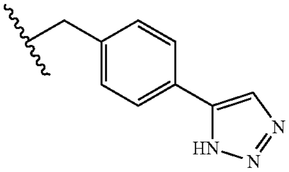 [SMILES: *Cc1ccc(-c2cnn[nH]2)cc1] | Me | 0.24 |
| 83 | 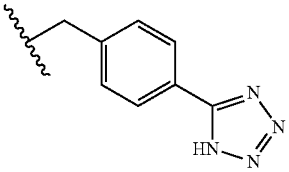 [SMILES: *Cc1ccc(-c2nnn[nH]2)cc1] | Me | 7.6 |
| 84 | 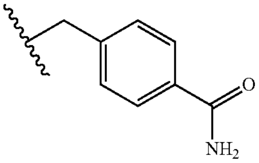 [SMILES: *Cc1ccc(C(N)=O)cc1] | Me | 6.8 |
| 85 | 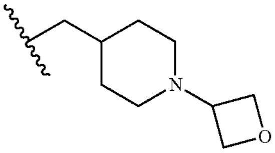 [SMILES: *CC1CCN(C2COC2)CC1] | Me | 15 |
| 86 | 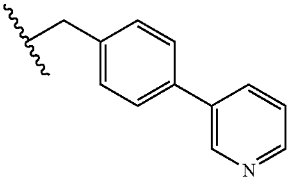 [SMILES: *Cc1ccc(-c2cccnc2)cc1] | F | 0.061 |
| 87 | 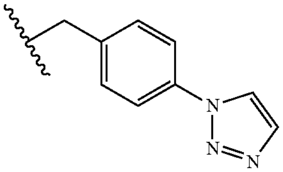 [SMILES: *Cc1ccc(-n2ccnn2)cc1] | F | 0.017 |

TABLE 4-continued

| Compound | $R^{10}$ | $R^4$ | $IC_{50}$ (μM) |
|---|---|---|---|
| 88 | 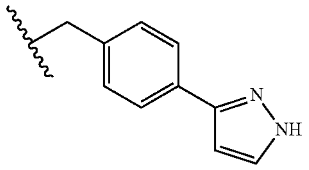 [SMILES: *Cc1ccc(-c2cc[nH]n2)cc1] | F | 0.15 |
| 89 | 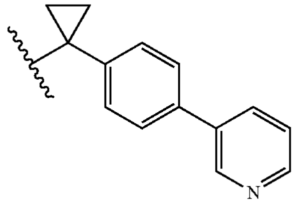 [SMILES: *C1(c2ccc(-c3cccnc3)cc2)CC1] | F | 0.034 |
| 90 | 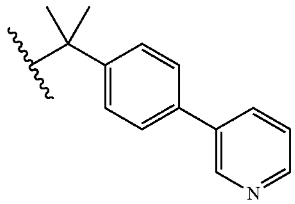 [SMILES: *C(C)(C)c1ccc(-c2cccnc2)cc1] | F | 0.19 |

EXAMPLE 12

This example provides characterization data for several embodiments of the invention.

2-(2-(difluoromethyl)phenyl)-5-fluoro-N-((1-(pyrazin-2-yDpiperidin-4-yl)methyl)pyrimidin-4-amine (NCGC00262647-01): LC-MS Retention Time: $t_1$ (Method 1)=3.274 min and $t_2$ (Method 2)=2.257 min; $^1H$ NMR (400 MHz, DMSO-$d_6$) δ ppm 8.26-8.32 (m, 2H), 8.05 (br. s., 3H), 7.77 (d, J=2.35 Hz, 2H), 7.59-7.67 (m, 2H), 4.34 (d, J=12.91 Hz, 2H), 3.37 (t, J=6.26 Hz, 2H), 2.84 (t, J=11.74 Hz, 2H), 1.95 (ddd, J=10.66, 6.95, 3.91 Hz, 1H), 1.73-1.84 (m, 2H), 1.12-1.27 (m, 2H); HRMS (ESI) m/z $(M+H)^+$ calcd. for $C_{21}H_{22}F_3N_6$, 415.1853. found 415.1865.

2-(2-isopropylphenyl)-5-methyl-N-(4-(pyridin-3-yl)benzyl)pyrimidin-4-amine (NCGC00250267-01): LC-MS Retention Time: $t_1$ (Method 1)=2.680 min and $t_2$ (Method 2)=1.466 min; $^1H$ NMR (400 MHz, DMSO-$d_6$) δ ppm 9.19-9.41 (m, 1 H), 8.89 (d, J=1.96 Hz, 1 H), 8.55-8.61 (m, 1 H), 8.30 (s, 1 H), 8.05-8.14 (m, 1 H), 7.70 (d, J=8.22 Hz, 2 H), 7.33-7.60 (m, 7 H), 4.82 (d, J=5.87 Hz, 2 H), 3.07 (dt, J=13.60, 6.70 Hz, 1 H), 2.25 (s, 3 H), 1.00 (s, 3 H), 0.98 (s, 3 H); HRMS (ESI) m/z $(M+H)^+$ calcd. for $C_{26}H_{27}N_4$, 395.2230. found 395.2242.

2-(2-isopropylphenyl)-5,6-dimethyl-N-(4-(pyridin-3-yl)benzyl)pyrimidin-4-amine (NCGC00253892-01): LC-MS Retention Time: $t_1$ (Method 1)=2.696 min and $t_2$ (Method 2)=1.497 min; $^1H$ NMR (400 MHz, DMSO-$d_6$) δ ppm 9.13-9.25 (m, 1 H), 8.89 (d, J=1.96 Hz, 1 H), 8.54-8.61 (m, 1H), 8.04-8.13 (m, 1H), 7.69 (d, J=8.22 Hz, 2H), 7.45-7.62 (m, 4H), 7.39 (d, J=8.22 Hz, 3H), 4.81 (d, J=5.87 Hz, 2H), 2.99 (dt, J=13.30, 6.65 Hz, 1H), 2.21 (s, 3H), 0.99 (s, 3H), 0.98 (s, 3H); HRMS (ESI) m/z $(M+H)^+$ calcd. for $C_{27}H_{29}N_4$, 409.2387. found 409.2397.

2-(2-isopropylphenyl)-N,5-dimethyl-N-(4-(pyridin-3-yl)benzyl)pyrimidin-4-amine (NCGC00262313-01): LC-MS Retention Time: $t_1$ (Method 1)=2.702 min and $t_2$ (Method 2)=3.911 min; $^1H$ NMR (400 MHz, DMSO-$d_6$) δ ppm 8.89-8.96 (m, 1H), 8.57-8.63 (m, 1H), 8.30 (s, 1H), 8.11-8.18 (m, 1H), 7.74 (d, J=8.22 Hz, 2H), 7.45-7.59 (m, 4H), 7.30-7.44 (m, 3H), 5.07 (s, 2H), 3.18 (dd, J=12.52, 5.87 Hz, 1H), 1.04 (br. s., 3H), 1.03 (br. s., 3H); HRMS (ESI) m/z $(M+H)^+$ calcd. for $C_{27}H_{29}N_4$, 409.2387. found 409.2389.

2-(2-isopropylphenyl)-N-(4-(pyridin-3-yl)benzyl)furo[3,2-d]pyrimidin-4-amine (NCGC00253883-01): LC-MS Retention Time: $t_1$ (Method 1)=2.706 min and $t_2$ (Method 2)=4.214 min; $^1H$ NMR (400 MHz, DMSO-$d_6$) δ ppm 9.46 (br. sJ=1.96 Hz, 1H), 8.95 (d, J=1.96 Hz, 1 H), 8.63 (d, J=5.09 Hz, 1H), 8.47 (s, 1H), 8.23 (d, J=7.83 Hz, 1H), 7.73 (d, J=8.22 Hz, 2H), 7.62 (dd, J=7.83, 5.09 Hz, 1H), 7.40-7.53 (m, 5H), 7.24-7.33 (m, 1H), 7.12 (d, J=1.96 Hz, 1H), 4.86 (d, 1=5.87 Hz, 2H), 3.31 (ddd, J=13.50, 7.04, 6.85 Hz, 1H), 1.05 (s, 3H), 1.03 (s, 3H); HRMS (ESI) m/z $(M+H)^+$ calcd. for $C_{27}H_{25}N_4O$, 421.2023. found 421.2011.

EXAMPLE 13

This example demonstrates the results of cytotoxicity assays for an embodiment of the invention.

Cytotoxicity assays were run as described in Example 6 using the cisplatin-sensitive NSCLC H460 cell line and the osteosarcoma U2OS cell line. For the H460 cells, a 1:4 combination of cisplatin and compound 81 killed cells with an $EC_{50}$ of 74 nM. For the U2OS cells, cisplatin alone killed cells with an $EC_{50}$of 0.629 μM; compound 81 killed cells with an $EC_{50}$ of >10 μM; 1:1 and 1:4 combinations of cisplatin and compound 81 killed cells with $EC_{50}$ values of 0.308 μM and 0.088 μM, respectively.

EXAMPLE 14

This example demonstrates a synthesis of a compound in accordance with an embodiment of the invention.

N-(4-(1H-1,2,3-triazol-1-yl)benzyl)-2-chloro-5-methyl-pyrimidin-4-amine 4-aminobenzonitrile (1.0 g, 8.46 mmol), trifluoroacetic acid (TFA) (0.65 mL, 8.46 mmol) in acetonitrile (70 mL) was stirred at room temperature for 5 min. The reaction mixture was cooled to 0° C. in a salt ice bath before the dropwise addition of tert-butyl nitrite (1.51 mL, 12.70 mmol) followed by azidotrimethylsilane (1.35 mL, 10.16 mmol). This reaction mixture was stirred for 30 min at 0° C., allowed to warm to room temperature (rt) before pouring into ethyl acetate (50 mL) and water (75 mL). The water layer was extracted (2×) with ethyl acetate, the organic layers were combine and washed (1×) with brine. The organic layer was dried over $Na_2SO_4$, filtered, and concentrated under reduced pressure to give 1.22 g of the product as a reddish brown solid in a 98% yield. The compound was used as is in the next reaction: LC-MS Retention Time (Method 2: 3 min)=3.331 min.

4-azidobenzonitrile (1.22 g, 8.33 mmol), sodium ascorbate (1.32 g, 6.66 mmol), copper (II) sulfate (93 mg, 0.0.58 mmol), and ethynyltrimethylsilane (6.20 mL, 50.0 mmol), was heated in DMSO/water (80 mL/40 mL) to 80° C. in a sealed tube for 24 h. The reaction was allowed to cool to rt and poured into ethyl acetate, and washed (3×) with 100 mL water. The organic layer was dried over $Na_2SO_4$, filtered, and concentrated under reduced pressure. The residue was taken up in acetonitrile (16 mL), and TFA (0.64 mL, 8.33 mmol) and heated to reflux for 1.5 h. After this time, the reaction was cooled to rt and poured in to ethyl acetate (30 mL), washed (2×) with saturated sodium bicarbonate, dried over $Na_2SO_4$, filtered, and concentrated. The residue was placed on a reverse phase flash system for purification (gradient 20-100% acetonitrile w/0.1% TFA in water w/0.1% TFA). LC-MS Retention Time (Method 2: 3 min)= 2.671 min; $^1H$ NMR (400 MHz, DMSO-$d_6$) δ 8.98 (d, J=1.26 Hz, 1H), and 8.22-8.00 (m, 5H); $^{13}C$ NMR (101 MHz, $CDCl_3$) δ 139.81, 135.13, 133.94, 133.14, 121.64, 120.71, 120.69, 117.68, and 112.40. m/z $(M+H)^+=171.1$. The above-mentioned 4-(1H-1,2,3-triazol-1-yl)benzonitrile (1.2 g, 7.05 mmol), TFA (0.60 mL 7.8 mmol), was dissolved in methanol (100 mL)/DMF (10 mL) and passed through a H-Cube Pro® flow reactor using a 10% Pd/C 70 mm Catcart, at 50 bar and 50° C. Once the reaction is complete the MeOH was concentrated and the crude used in the next reaction sequence. LC-MS Retention Time (Method 2: 3 min)=1.386 min (m/z $(M+H)^+=174.2$).

N-(4-(1H-1,2,3-triazol-1-yl)benzyl)-2-chloro-5-methylpyrimidin-4-amine (4-(1H-1,2,3-triazol-1-yl)phenyl)methanamine, TFA (7.05 mmol), 2,4-dichloro-5-methylpyrimidine (1.16 g, 7.05 mmol), triethylamine (3.0 mL, 21.3 mmol), was heated overnight to 100° C. in DMF (25 mL). The completed reaction was poured into water (30 mL) and extracted with ethyl acetate. The ethyl acetate layer was washed (2×) with water (1×) with saturated sodium bicarbonate, dried over $Na_2SO_4$, filtered, and concentrated. The residue was purified on a reverse phase flash system (gradient 10-100% acetonitrile w/0.1% TFA in water w/0.1% TFA) to give 0.19 g of desired product. $^1H$ NMR (400 MHz, DMSO-$d_6$) δ 8.76 (d, J=1.17 Hz, 1H), 7.97-7.90 (m, 2H), 7.86-7.80 (m, 3H), 7.54-7.48 (m, 2H), 4.63 (d, J=5.98 Hz, 2H), and 2.18-1.75 (m, 3H); $^{13}C$ NMR (101 MHz, DMSO-$d_6$) δ 162.60, 157.80, 154.97, 140.20, 135.90, 134.78, 129.01, 123.61, 120.61, 113.64, 43.54, and 13.50; LC-MS Retention Time (Method 2: 3 min)=2.770 min; m/z $(M+H)^+=301.1$.

N-(4-(1H-1,2,3-triazol-1-yl)benzyl)-2-(2-isopropylphenyl)-5-methylpyrimidin-4-amine (81)

N-(4-(1H-1,2,3-triazol-1-yl)benzyl)-2-chloro-5-methylpyrimidin-4-amine (0.19 g, 0.63 mmol) was combined with 2-isopropylphenylboronic acid (0.31 g, 1.90 mmol), sodium carbonate (2.0 M in water, 1.23 mL, 2.53 mmol), and DPP-Pd Silicycle® 0.26 mmol/g (0.30 g) in DMF (4.50 mL). The reaction was heated at 150° C. for 30 min in a Biotage Initiator® microwave reactor. The resulting mixture was filtered over celite and purified by HPLC (gradient 20-100% acetonitrile w/0.1% TFA in water w/0.1% TFA) to yield, after lyophilization, N-(4-(1H-1,2,3-triazol-1-yl)benzyl)-5-methyl-2-(2-isopropylphenyl)-pyrimidin-4-amine as a TFA salt (0.01 g, 0.02 mmol, 30%): LC-MS Retention Time (Method 1: 7 min)=2.938 min and (Method 2: 3 min)=1.756 min; $^1H$ NMR (400 MHz, $CDCl_3$) δ 8.82 (dd, J=7.9, 3.4 Hz, 1H), 8.02-7.93 (m, 2H), 7.76 (d, J=1.4 Hz, 1H), 7.64-7.56 (m, 2H), 7.51-7.33 (m, 5H), 7.25-7.17 (m, 1H), 4.88 (d, J=5.9 Hz, 2H), 3.19 (p, J=6.8 Hz, 1H), 2.22 (s, 3H), 1.10 (d, J=1.2 Hz, 3H) and 1.09-1.07 (m, 4H); $^{13}C$ NMR (100 MHz, $CDCl_3$) δ 162.02, 160.18, 148.00, 140.63, 138.03, 136.14, 134.35, 134.28, 131.89, 130.34, 129.25, 129.00, 126.61, 126.04, 122.04, 121.99, 120.74, 113.81, 44.62, 29.43, 23.95, 13.71 and 13.67; HRMS (ESI) m/z $(M+H)^+$ calcd. for $C_{23}H_{25}N_6$, 385.2135. found 385.2146.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I):

(I)

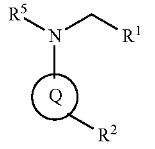

wherein Q is

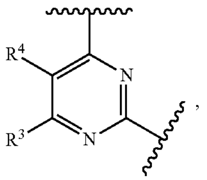

wherein $R_1$ is selected from aryl,

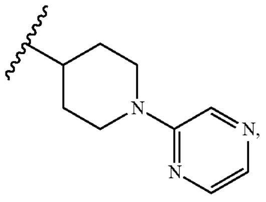

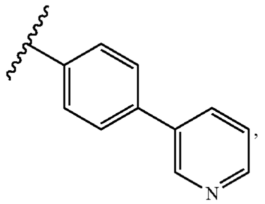

-continued

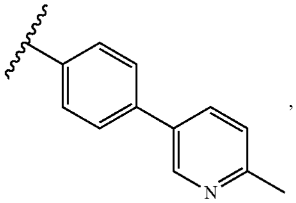, 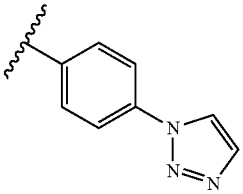,

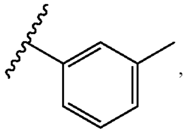, 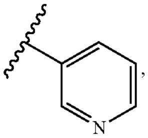, 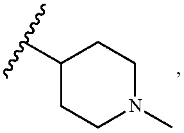,

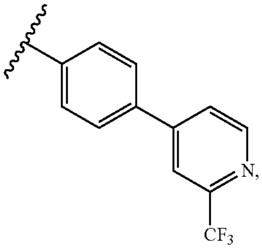 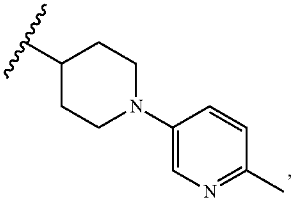,

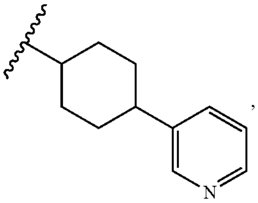, 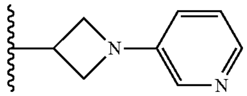,

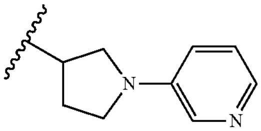, 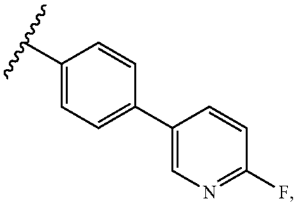

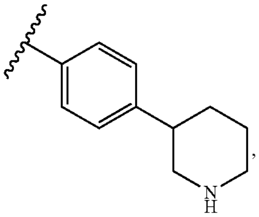, 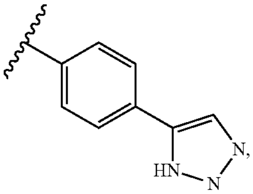

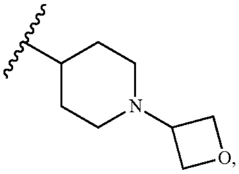 and 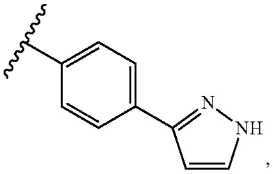, $R^2$ is selected from

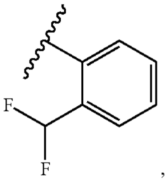, 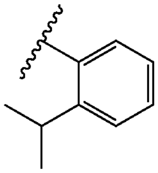,

-continued

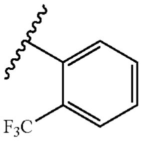, 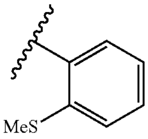,

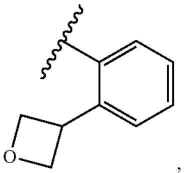, 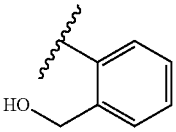,

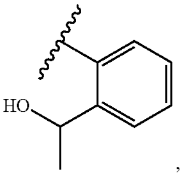, 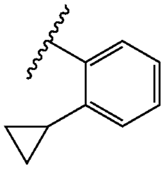, and

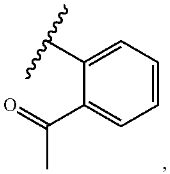, $R^3$ is selected from hydrogen and alkyl, $R^4$ is selected from hydrogen, alkyl, alkoxy, amino, alkylamino, dialkylatnino, alkyithio, and halo, and $R^5$ is hydrogen or alkyl, a deuterated derivative thereof, or a pharmaceutically acceptable salt thereof.

2. The compound, deuterated derivative thereof, or salt of claim 1, wherein $R^5$ is hydrogen, $R^3$ is selected from hydrogen and methyl, $R_4$ is selected from hydrogen, methyl, methoxy, amino, dimethylamino, methyithio, and halo.

3. The compound, deuterated derivative thereof or salt of claim 1, wherein $R^1$ is

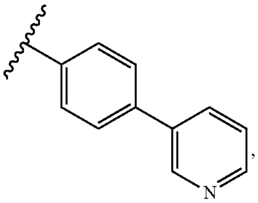 [SMILES: *c1ccc(-c2cccnc2)cc1]

$R^3$ is hydrogen, $R^4$ is methyl, and $R^2$ is

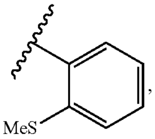, 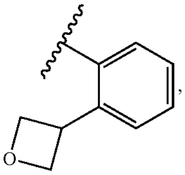, 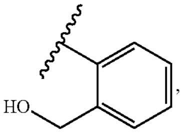,

-continued
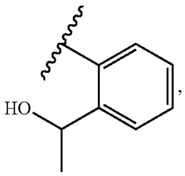, 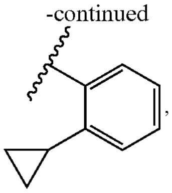, or 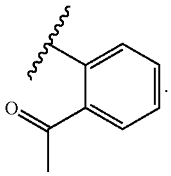.
4. A pharmaceutical composition comprising a compound, deuterated derivative thereof, or salt of claim 1 and a pharmaceutically acceptable carrier.
* * * * *